(12) United States Patent
Najafi et al.

(10) Patent No.: US 11,850,416 B2
(45) Date of Patent: Dec. 26, 2023

(54) METHOD OF MANUFACTURING A PROBE ARRAY

(71) Applicant: The Regents of the University of Michigan, Ann Arbor, MI (US)

(72) Inventors: Khalil Najafi, Ann Arbor, MI (US); Seyed Amin Sandoughsaz Zardini, Ann Arbor, MI (US); Daniel Egert, San Francisco, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1084 days.

(21) Appl. No.: 16/449,012

(22) Filed: Jun. 21, 2019

(65) Prior Publication Data
US 2019/0388678 A1    Dec. 26, 2019

Related U.S. Application Data

(60) Provisional application No. 62/688,800, filed on Jun. 22, 2018.

(51) Int. Cl.
*A61N 1/05* (2006.01)
*A61B 5/00* (2006.01)

(52) U.S. Cl.
CPC ............ *A61N 1/0529* (2013.01); *A61B 5/685* (2013.01); *A61B 2562/125* (2013.01); *A61B 2562/168* (2013.01); *Y10T 29/49002* (2015.01)

(58) Field of Classification Search
CPC .............................. A61N 1/0529; A61B 5/685; A61B 2562/125; A61B 5/24; Y10T 29/49002; A61M 5/158
See application file for complete search history.

(56) References Cited

U.S. PATENT DOCUMENTS

| | | | |
|---|---|---|---|
| 9,224,750 B1* | 12/2015 | Yeh | H01L 21/02164 |
| 11,045,142 B1* | 6/2021 | Windmiller | A61M 37/0015 |
| 2004/0011134 A1* | 1/2004 | Sato | H10N 30/092 29/25.35 |

(Continued)

OTHER PUBLICATIONS

McAllister et al., PANS, vol. 100, Nov. 2003, pp. 13755-13760 (Year: 2003).*

(Continued)

*Primary Examiner* — Peter Dungba Vo
*Assistant Examiner* — Jose K Abraham
(74) *Attorney, Agent, or Firm* — Reising Ethington P.C.

(57) ABSTRACT

Various methods of manufacture can produce three-dimensional, high density, high-electrode probe arrays that can advantageously be used in neural-based applications. In one example, deep reactive ion etched (DRIE) ultra-high aspect ratio holes are etched in silicon and refilled with multiple films to a high density array of individual probes, each probe having individual recording and/or stimulation sites or tips. Using a DRIE lag effect technique can help control tip sharpness and electrode length, allowing for narrow, long, and dense needles to be formed side-by-side in a single array. In some examples, multimodal probe arrays are manufactured, with some probes having a recording/stimulating site, other probes having a waveguide, and yet other probes having a microfluidic channel.

27 Claims, 28 Drawing Sheets

(56) References Cited

U.S. PATENT DOCUMENTS

| | | | | |
|---|---|---|---|---|
| 2006/0215379 | A1* | 9/2006 | Zollo | H05K 1/185 156/295 |
| 2007/0267218 | A1* | 11/2007 | Kimura | H01L 21/486 257/E23.178 |
| 2008/0063866 | A1* | 3/2008 | Allen | H05K 1/02 428/401 |
| 2011/0089967 | A1* | 4/2011 | Kim | G01R 3/00 156/89.18 |
| 2011/0162204 | A1* | 7/2011 | Reiss | G11B 23/40 29/874 |
| 2011/0224515 | A1* | 9/2011 | Mir | A61B 5/15151 600/317 |
| 2011/0313298 | A1* | 12/2011 | Rylander | A61B 5/0059 600/478 |
| 2012/0310067 | A1* | 12/2012 | Najafi | A61B 5/685 607/116 |
| 2013/0144217 | A1* | 6/2013 | Ross | B29C 59/002 604/173 |
| 2013/0165872 | A1* | 6/2013 | Stumber | A61M 37/0015 604/272 |
| 2013/0338627 | A1* | 12/2013 | Rylander | A61B 18/20 604/501 |
| 2013/0341701 | A1* | 12/2013 | Blomme | H01L 29/7889 438/591 |
| 2016/0014908 | A1* | 1/2016 | Rathburn | C23C 18/1653 228/176 |
| 2016/0086971 | A1* | 3/2016 | Yeh | H01L 29/511 438/269 |
| 2016/0158514 | A1* | 6/2016 | Stoeber | A61M 37/0015 427/2.28 |
| 2016/0256091 | A1* | 9/2016 | Cho | A61B 5/14865 |
| 2017/0312535 | A1* | 11/2017 | Kim | A61N 2/006 |
| 2017/0347925 | A1* | 12/2017 | Wang | A61B 5/157 |
| 2019/0125223 | A1* | 5/2019 | Wang | A61B 5/14532 |

OTHER PUBLICATIONS

Tang et.al., 2017 IEEE International Conference on Micro Electro Mechanical Systems (MEMS), p. 700-703 (Year: 2017).*
Akin, Tayfun, Khalil Najafi, and Robert M. Bradley. "A wireless implantable multichannel digital neural recording system for a micromachined sieve electrode." IEEE Journal of solid-state circuits 33, No. 1 (1998): 109-118.
P.K. Campbell, K.E. Jones, R.J. Huber, K.W. Horch, and R.A. Normann, "A Silicon based, three-dimensional neural interface: manufacturing processes for an intracortical electrode array," IEEE Trans. Biomed. Eng., vol. 38, No. 8, pp. 758-768, 1991.
D. E. Gunning, J. M. Beggs, W. Dabrowski, P. Hottowy, C. J. Kenney, A. Sher, A. M. Litke, and K. Mathieson. "Dense arrays of micro-needles for recording and electrical stimulation of neural activity in acute brain slices." J. Neural Eng., vol. 10, 016007, 2013.
K. Deisseroth, G. Feng, A. K. Majewska, G. Miesenbock, A. Ting, M. J. Schnitzer, "Next-Generation Optical Technologies for Illuminating Genetically Targeted Brain Circuits," J. Neuroscience, 2006, 26 (41), 10380-6.
M. Ghovanloo and K. Najafi, (Jan. 2007) "Towards a button-sized 1024-site wireless cortical microstimulating array," in Handbook of Neural Engineering, Ed. M. Akay, Ch. 23, Hoboken: John Wiley & Sons, Inc.
A.C. Hoogerwerf and K.D. Wise, "A Three-dimensional microelectrode array for chronic neural recording," IEEE Trans. Biomed. Eng., vol. 41, No. 12, pp. 1136-1146, 1994.
T.D. Yoshida Kozal, N.B. Langhals, P.R. Patel, X. Deng, H. Zhang, K.L. Smith, J. Lahann, N.A. Kotov, and D.R. Kipke, "Ultrasmall implantable composite microelectrodes with bioactive surfaces for chronic neural interfaces," Nat. Mater., vol. 11, pp. 1065-1073, 2012.
P. Ledochowitsch, R. J. Felus, R.R. Gibboni, A. Miyakawa, S. Bao, and M.M. Maharbiz, "Fabrication and testing of a large area, high density, Parylene MEMS μECOG array," in Proc IEEE MEMS, Cancun, Mexico, Jan. 2011.
L. Luan, et al., "Ultraflexible nanoelectronic probes form reliable, glial scar-free neural integration," Sci. Adv., 3, p. e1601966, 2017.
J. Meyer, T. Stieglitz, O. Scholz, W. Haberer, and H. Beutel, "High density interconnects and flexible hybrid assemblies for active biomedical implants," IEEE Trans. Adv. Packaging, vol. 24, No. 3, pp. 366-374, 2001.
S.A. Nikles, R.M. Bradley, S. Bledsoe, and K. Najafi. "Design and testing of conductive polysilicon beam leads for use in a high-density biomedical connector." Journal of Micromechanics and Microengineering 14, No. 7, p. 957, 2004.
http://www.omnetics.com/products/neuro-connectors/nano-strip-connectors, accessed Jan. 19, 2023.
J. Patel, E. W. Schomburg, A. Berényi, S. Fujisawa, and G. Buzsáki, "Local Generation and Propagation of Ripples along the Septotemporal Axis of the Hippocampus," Journal of Neuroscience, vol. 33, No. 43, pp. 17029-17041, 2013.
P.R. Patel, K. Na, H. Zhang, T.D.Y. Kozai, N.A. Kotov, E. Yoon, and C.A. Chestek, "Insertion of linear 8.4μm diameter 16 channel carbon fiber electrode arrays for single unit recordings," J. Neural Eng., vol. 12, art. No. 046009, 2015.
B. C. Raducanu, et al., "Time multiplexed active neural probe with 1356 parallel recording sites," Sensors, vol. 17, No. 10, 2388, 2017.
G. Rios, E.V. Lubenov, D. Chi, M.L. Roukes, and A.G. Siapas, "Nanofabricated neural probes for dense 3-D recordings of brain activity," Nano Lett., vol. 16, pp. 6857-6862, 2016.
N. Sadeh, E. Oni-Biton, and M. Segal, "Acute Live/Dead Assay for the Analysis of Toxic Effects of Drugs on Cultured Neurons," Bio-protocol, vol. 6, No. 15, pp. 12404-12411, 2016.
J. Scholvin, J. P. Kinney, J. G. Bernstein, C. Moore-Kochlacs, N. Kopell, C. G. Fonstad, and E. S. Boyden, "Close-packed silicon microelectrodes for scalable spatially oversampled neural recording," IEEE Trans. Biomed. Eng., vol. 63, No. 1, pp. 120-130, 2016.
J.P. Seymour, F. Wu, K.D. Wise, E. Yoon, State-of-the-art MEMS and microsystem tools for brain research, Microsyst. Nanoeng., vol. 3, 16066, 2017.
Sodagar, Amir M., Gayatri E. Perlin, Ying Yao, Khalil Najafi, and Kensall D. Wise. "An implantable 64-channel wireless microsystem for single-unit neural recording." IEEE Journal of Solid-State Circuits 44, No. 9 (2009): 2591-2604.
I.H. Stevenson and K. P. Kording, "How advances in neural recording affect data analysis," Nat. Neurosci., vol. 14, No. 2, pp. 139-142, 2011.
P. Stice, A. Gilletti, A. Panitch, and J. Muthuswamy, "Thin microelectrodes reduce GFAP expression in the implant site in rodent somatosensory cortex," J. Neural Eng., vol. 4, No. 2, pp. 42-53, 2007.
B.A. Strange, M. P. Witter, E. S. Lein, and E. I. Moser, "Functional organization of the hippocampal longitudinal axis," in Nat. Rev. Neurosci., vol. 15(10), pp. 655-669, 2014.
Y. Tang, A. Sandoughsaz, K. Najafi, "Ultra high aspect-ratio and thick deep silicon etching (UDRIE)," in Proc IEEE MEMS, Las Vegas, Nevada, Jan. 2017.
R.P. von Metzen, T. Stieglitz, "A Wireless System for Monitoring Polymer Encapsulations," 2007 29th Annual International Conference of the IEEE Engineering in Medicine and Biology Society, 6600-6603, 2007.
H. A. C. Wark, et al., "A new high-density (25 electrodes/mm2) penetrating microelectrode array for recording and stimulating sub-millimeter neuroanatomical structures," J. Neural Eng., vol. 10, No. 4, 045003, 2013.
C. Xie, J. Liu, T.Fu, X. Dai, W. Zhou, and C.M. Lieber, "Three-dimensional macroporous nanoelectronic networks as minimally invasive brain probes," Nat. Mater., vol. 14, pp. 1286-1292, 2015.
Yao, Y., M. N. Gulari, B. Casey, J. A. Wiler, and K. D. Wise. "Silicon microelectrodes with flexible integrated cables for neural implant applications." In Neural Engineering, 2007. CNE'07. 3rd International IEEE/EMBS Conference on, pp. 398-401, 2007.
H. Yu, and K. Najafi. "Circuitry for a wireless microsystem for neural recording microprobes." In Engineering in Medicine and Biology Society, 2001. Proceedings of the 23rd Annual International Conference of the IEEE, vol. 1, pp. 761-764. IEEE, 2001.

(56) References Cited

OTHER PUBLICATIONS

T. Akin, B. Ziaie, S.A. Nikles, and K. Najafi. "A modular micromachined high-density connector system for biomedical applications." IEEE transactions on biomedical engineering 46, No. 4, pp. 471-480, 1999.

Aktakka, Ethem Erkan, Jong-Kwan Woo, Daniel Egert, Robert JM Gordenker, and Khalil Najafi. "A microactuation and sensing platform with active lockdown for in situ calibration of scale factor drifts in dual-axis gyroscopes." IEEE/ASME Transactions on Mechatronics 20, No. 2 (2015): 934-943.

C.S. Bjornsson, S.J. Oh, Y.A. Al-Kofahi, Y.J. Lim, K.L. Smith, J.N. Turner, S.De, B. Roysam, W. Shain, and S.J. Kim, "Effects of insertion conditions on tissue strain and vascular damage during neuroprosthetic device insertion," J. Neural Eng., vol. 3, No. 3, pp. 196-207, 2006.

A. Borna, and K. Najafi. "A low power light weight wireless multichannel microsystem for reliable neural recording." IEEE Journal of Solid-State Circuits 49, No. 2, pp. 439-451, 2014.

K. Deisseroth, "Optogenetics," Nat. Methods, vol. 8, No. 1, pp. 26-29, 2011.

D.J. Edell, "Insulating biomaterials." In Neuroprosthetics: Theory and Practice, pp. 517-579. 2004.

J.A. Gregory, A. Borna, R. Sabyasachi, X. Wang, B. Lewandowski, M. Schmidt, and K. Najafi, "Low-cost wireless neural recording system and software." In Engineering in Medicine and Biology Society, EMBC 2009. Annual International Conference of the IEEE, pp. 3833-3836. IEEE, 2009.

J.F. Hetke, K. Najafi, and K.D. Wise. "Flexible miniature ribbon cables for long-term connection to implantable sensors." Sensors and Actuators A: Physical 23, No. 1-3, pp. 999-1002, 1994.

J.F. Hetke, J. L. Lund, K. Najafi, K.D. Wise, and D.J. Anderson, "Silicon ribbon cables for chronically implantable microelectrode arrays," IEEE Trans. Biomed. Eng., vol. 41, No. 4, pp. 314-321, 1994.

J.F. Hetke, J.C. Williams, D.S. Pellinen, R.J. Vetter and D.R. Kipke, "3-D silicon probe array with hybrid polymer interconnect for chronic cortical recording," in Proc IEEE EMBS, Capri Island, Italy, Mar. 2003.

K. Imfeld, S. Neukom, A. Maccione, Y. Bornat, S. Martinoia, P. A. Farine, M. Koudelka-Hep and L. Berdondini, "Large-Scale, High-Resolution Data Acquisition System for Extracellular Recording of Electrophysiological Activity" IEEE Trans. Biomed. Eng., vol. 55, pp. 2064-2073, 2008.

S. Kisban, P. Janssen, S. Herwik, T. Stieglitz, O. Paul, and P. Ruther, "Hybrid microprobes for chronic implantation in the cerebral cortex," in Proc IEEE EMBS, Vancouver, British Columbia, Canada, Aug. 2008.

H. J. Lee, Y. Son, J. Kim, C. J. Lee, E. Yoon, and I. Cho, "A multichannel neural probe with embedded microfluidic channels for simultaneous in vivo neural recording and drug delivery," Lab chip, vol. 15, No. 6, pp. 1590-1597, 2015.

C. M. Lopez, et al., "A neural probe with up to 966 electrodes and up to 384 configurable channels in 0.13 μm SOI CMOS," IEEE Trans. Biomed. Cicruits Syst., vol. 11, No. 3, pp. 510-522, 2017.

K.A. Ludwig, N.B. Langhals, M.D. Joseph, S. M. Richardson-Burns, J. L. Hendricks, and D.R. Kipke, "Poly(3,4-ethylenedioxythiophene) (PEDOT) polymer coatings facilitate smaller neural recording electrodes," J. Neural Eng., vol. 8, No. 1, 014001, 2011.

B. Lustig, Y. Wang, and E. Pastalkova, "Oscillatory patterns in hippocampus under light and deep isoflurane anesthesia closely mirror prominent brain States in awake animals," Hippocampus, vol. 26, No. 1, pp. 102-109, 2016.

S.P. Marshall, W. Lin, P.R. Patel, A.J. Shih, C. A. Chestek, "Effects of geometry and material on the insertion of very small neural electrode," in Proc. EMBC, Orlando, Florida, USA, Aug. 2016.

Mohseni, Pedram, Khalil Najafi, Steven J. Eliades, and Xiaoqin Wang. "Wireless multichannel biopotential recording using an integrated FM telemetry circuit." IEEE Transactions on Neural Systems and Rehabilitation Engineering 13, No. 3, pp. 263-271, 2005.

K. Najafi, K.D. Wise, and T. Mochizuki, "A high-yield ICcompatible multichannel recording array," IEEE Trans. Electron Devices, vol. ED-32, No. 7, pp. 1206-1211, 1985.

K. Najafi and K.D. Wise, "An implantable multielectrode array with on-chip signal processing," IEEE J. Solid-State Circuits, vol. 21, No. 6, pp. 1035-1044, 1986.

K. Najafi, J. Hetke, "Strength Characterization of Silicon Microprobes in Neurophysiological Tissues," IEEE Trans. Biomed. Eng., vol. 37, No. 5, pp. 474-481, 1990.

K. Najafi, "Packaging of implantable microsystems," in Proc. IEEE Sensors Conf., Atlanta, Georgia, Oct. 2007.

K. Najafi, T.J. Harpster, H. Kim, U.S. Mitchell, W.C. Welch III, "Wafer Bonding," chapter in Comprehensive Microsystems, edited by Y. Gianchandani, Hans Zappe, and O. Tabata, Elsevier Publishers, 2008.

S.A., Nikles, K. Najafi, R.M. Bradley, and S. Bledsoe. "Reliability and contact resistance of polysilicon beam leads for use in a high-density connector." In Micro Electro Mechanical Systems, 2001. MEMS 2001. The 14th IEEE International Conference on, pp. 64-67. IEEE, 2001.

A. Nikles, D.S. Pellinen, J. Kitagawa, R.M. Bradley, D.R. Kipke, and K. Najafi. "Long term in vitro monitoring of polyimide microprobe electrical properties." In Engineering in Medicine and Biology Society, 2003. Proceedings of the 25th IEEE Annual International Conference of the IEEE, vol. 4, pp. 3340-3343, 2003.

S-Y Park, J. Cho, K. Na, and E. Yoon. "Toward 1024-channel parallel neural recording: Modular Δ-ΔΣ analog front-end architecture with 4.84 fJ/Cs· mm 2 energy area product." In VLSI Circuits (VLSI Circuits), 2015 Symposium on, pp. C112-C113. IEEE, 2015.

D.A. Schwarz, et al., "Chronic, wireless recordings of large-scale brain activity in freely moving rhesus monkeys," Nat. Methods, vol. 11, No. 6, pp. 670-679, 2014.

A.A. Sharp, A. M. Ortega, D. Restrepo, D. Curran-Everett, and K. Gall, "In Vivo penetration mechanics and mechanical properties of mouse brain tissue at micrometer scales," IEEE Trans. Biomed. Eng., vol. 56, No. 1, pp. 45-53, 2009.

H. Shin, H. J. Lee, U. Chae, H. Kim, J. Kim, N. Choi, J. Woo, Y. Cho, C. J. Lee, E. Yoon, I. Cho, "Neural probes with multi-drug delivery capability"; Lab on a Chip, 2015, 15, 3730.

M. Cheng, L. Yao, K.L. Tan, R. Lim, P. Li, and W. Chen, "3D probe array integrated with a front-end 100-channel neural recording ASIC," J. Micromech. Microeng., vol. 24, No. 12, 125010, 2014.

\* cited by examiner

Variable Shank Diameter

Variable Pitch/Density

Variable Length
Variable Shank Diameter

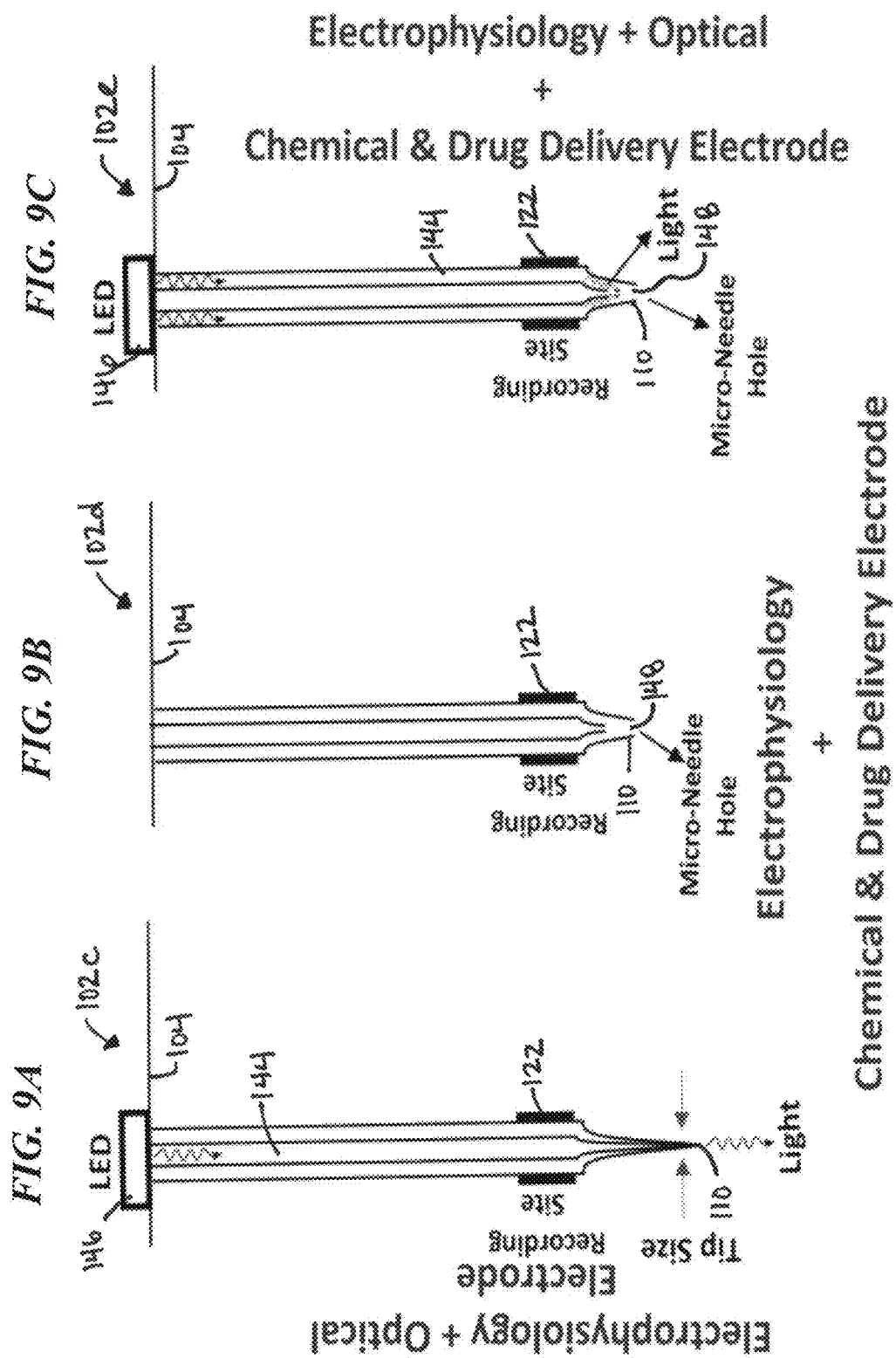

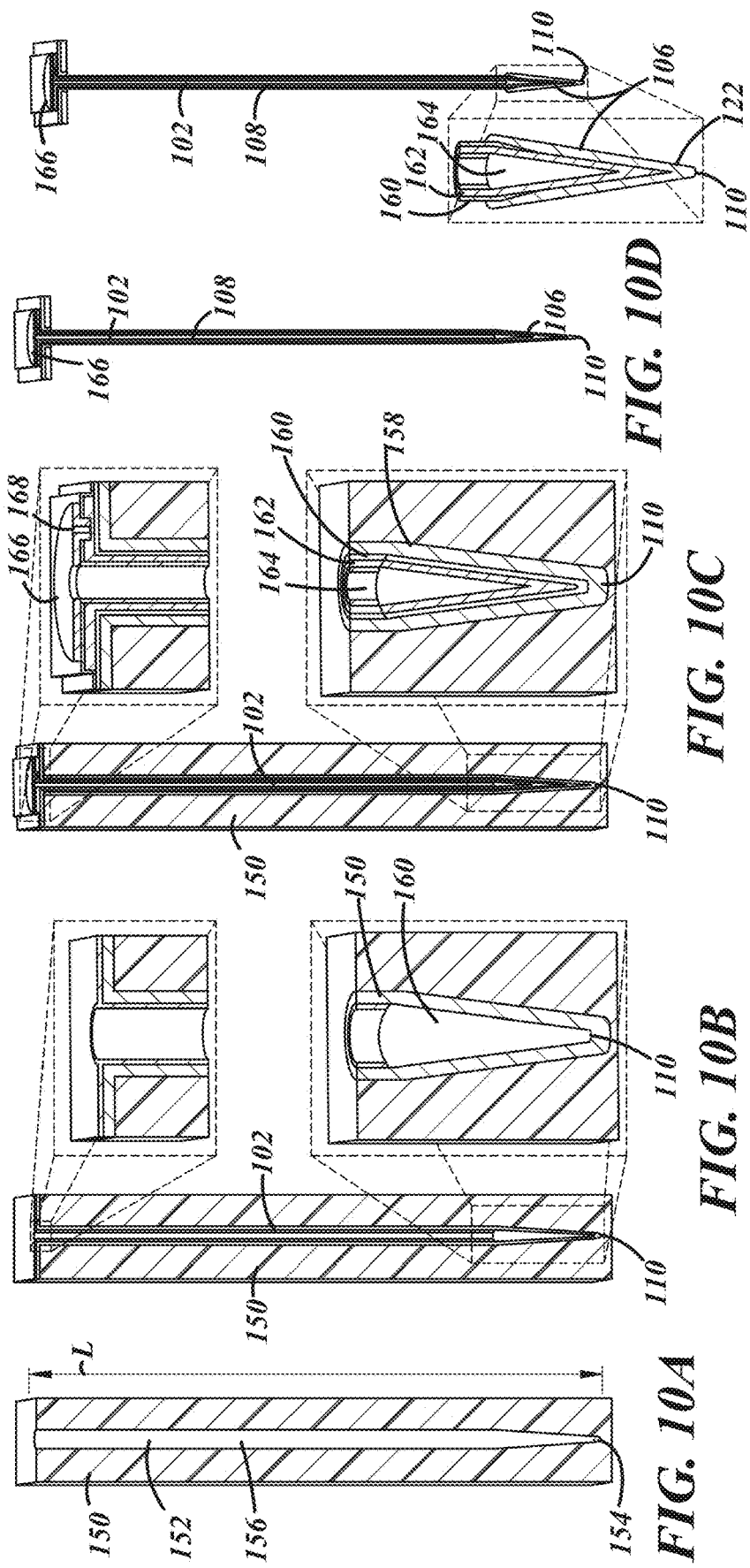

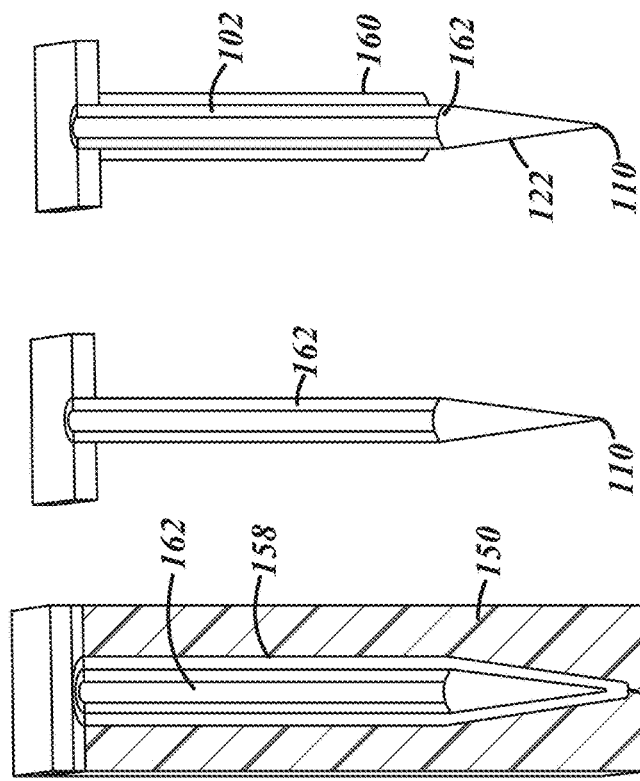
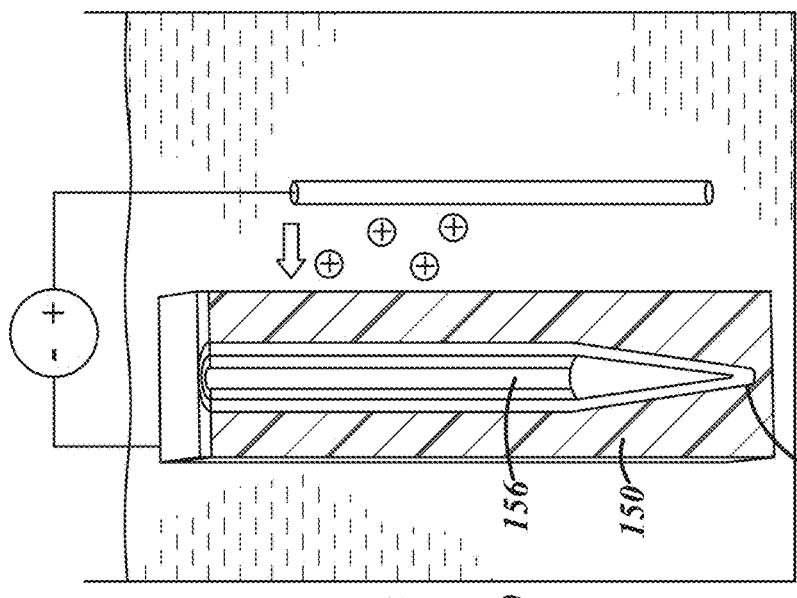
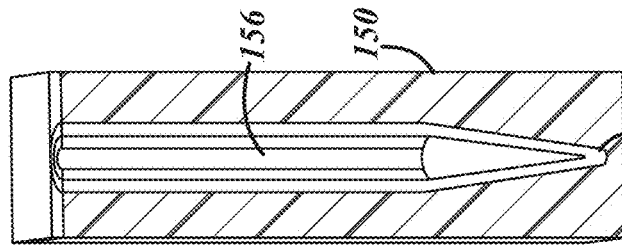
FIG. 12A  FIG. 12B  FIG. 12C  FIG. 12D  FIG. 12E

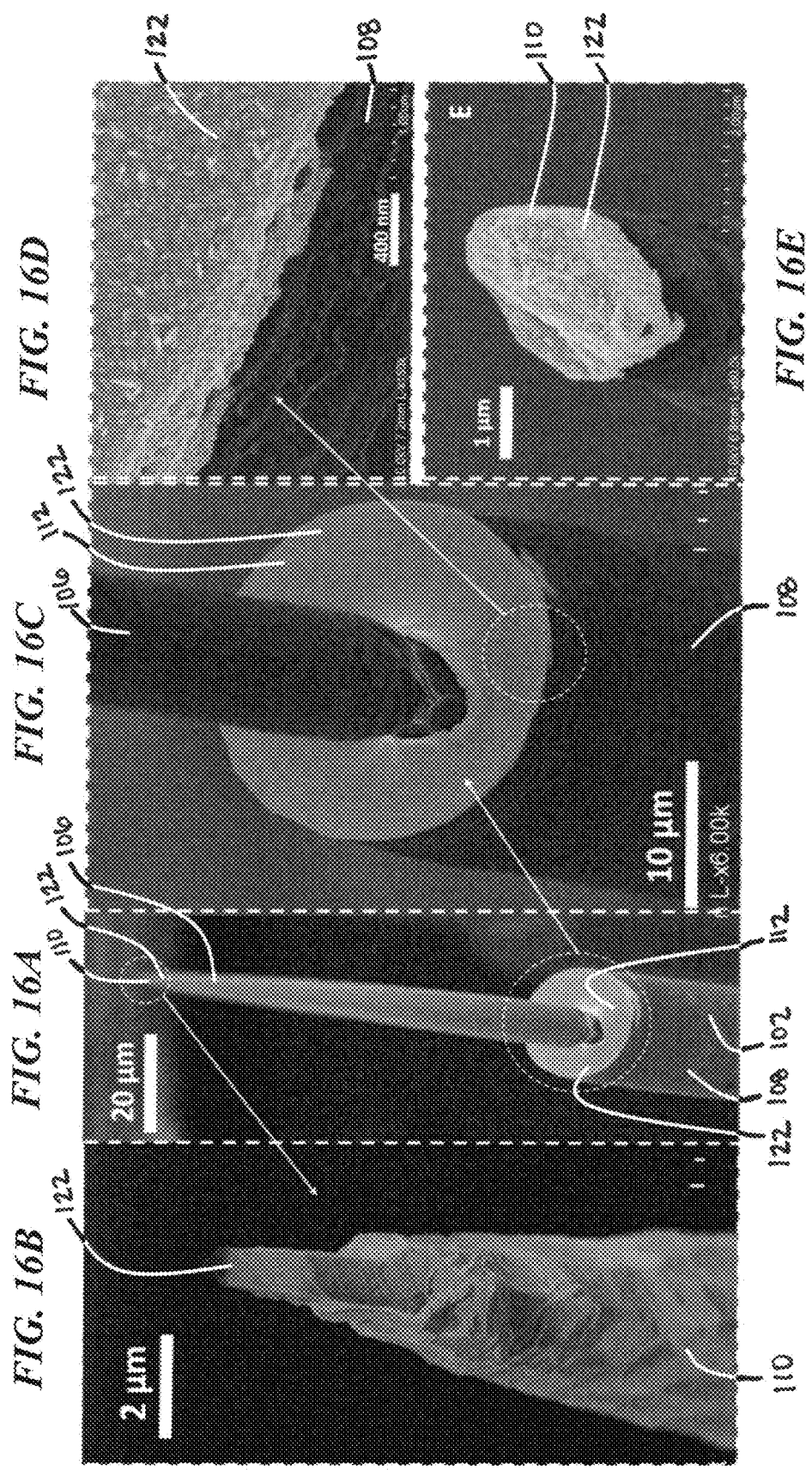

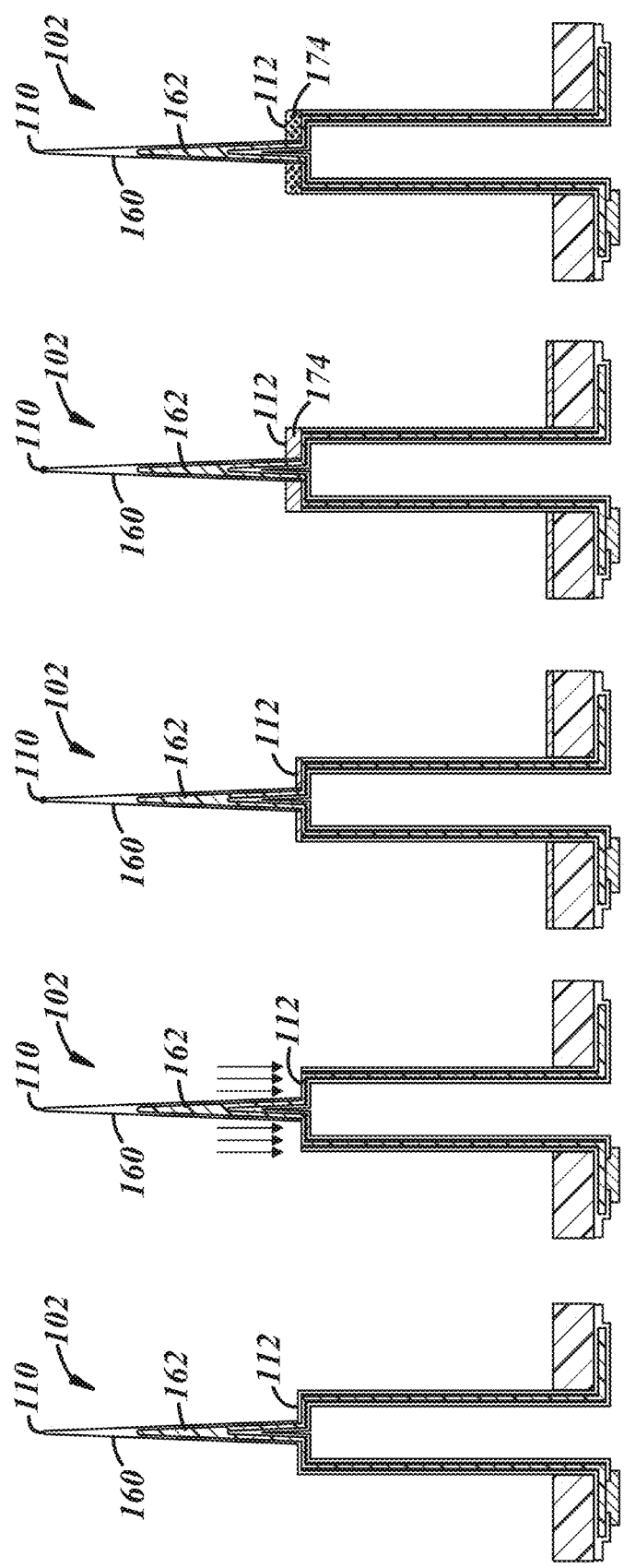

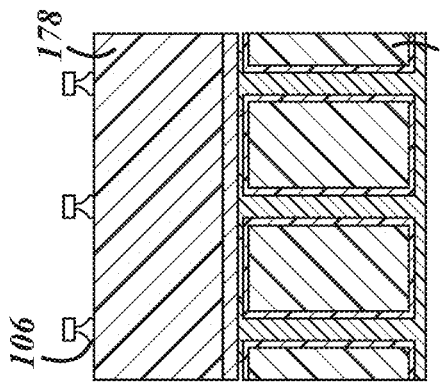
FIG. 19A
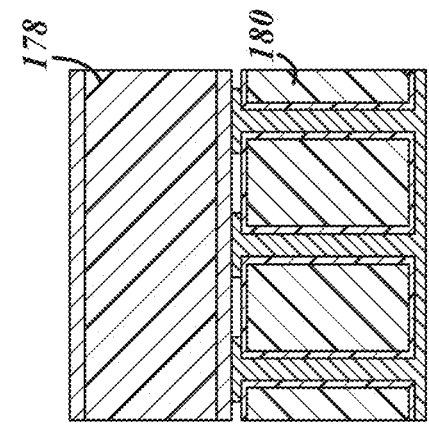
FIG. 19B
FIG. 19C
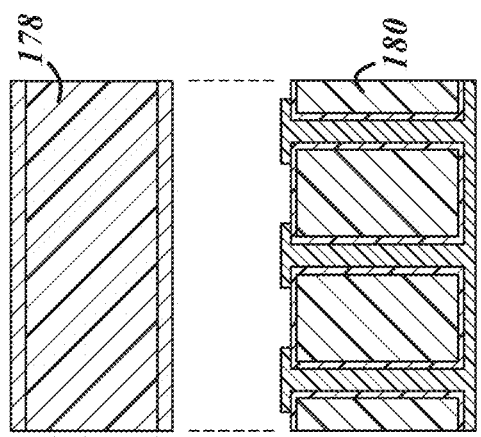
FIG. 19D
FIG. 19E
FIG. 19F

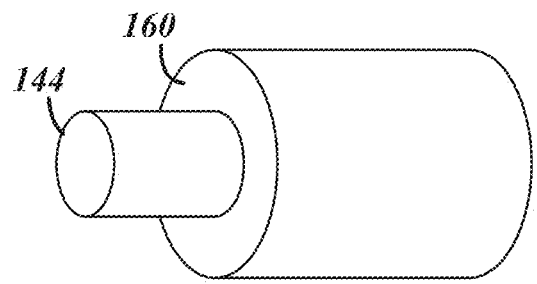
FIG. 20
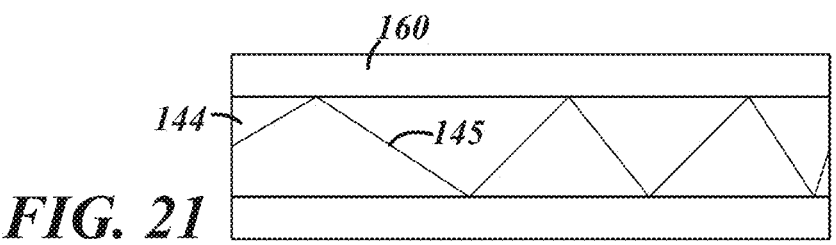
FIG. 21
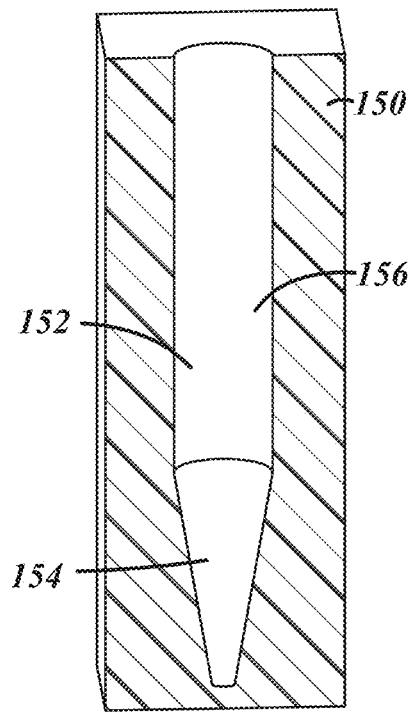
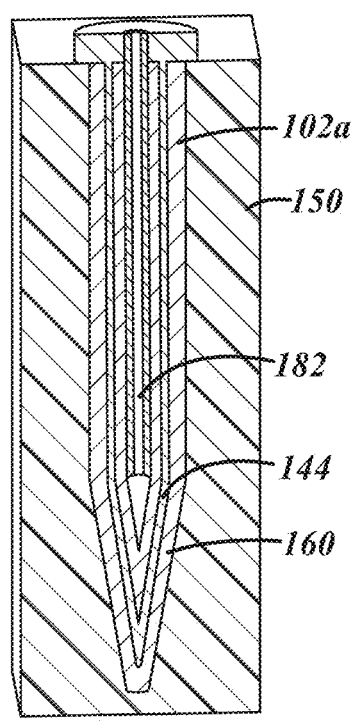
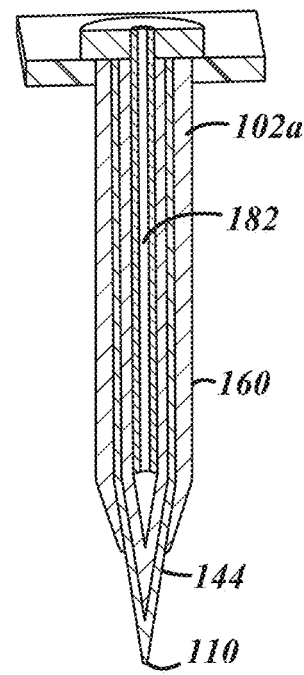
FIG. 22A    FIG. 22B    FIG. 22C

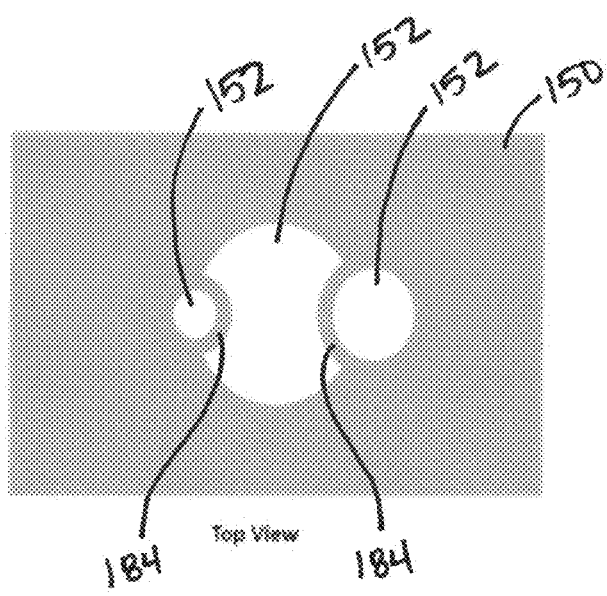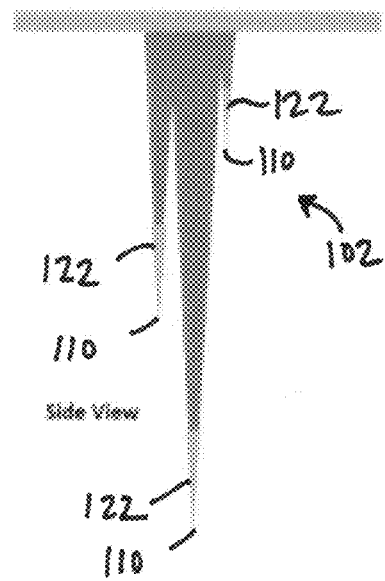
*FIG. 25A*  *FIG. 25B*

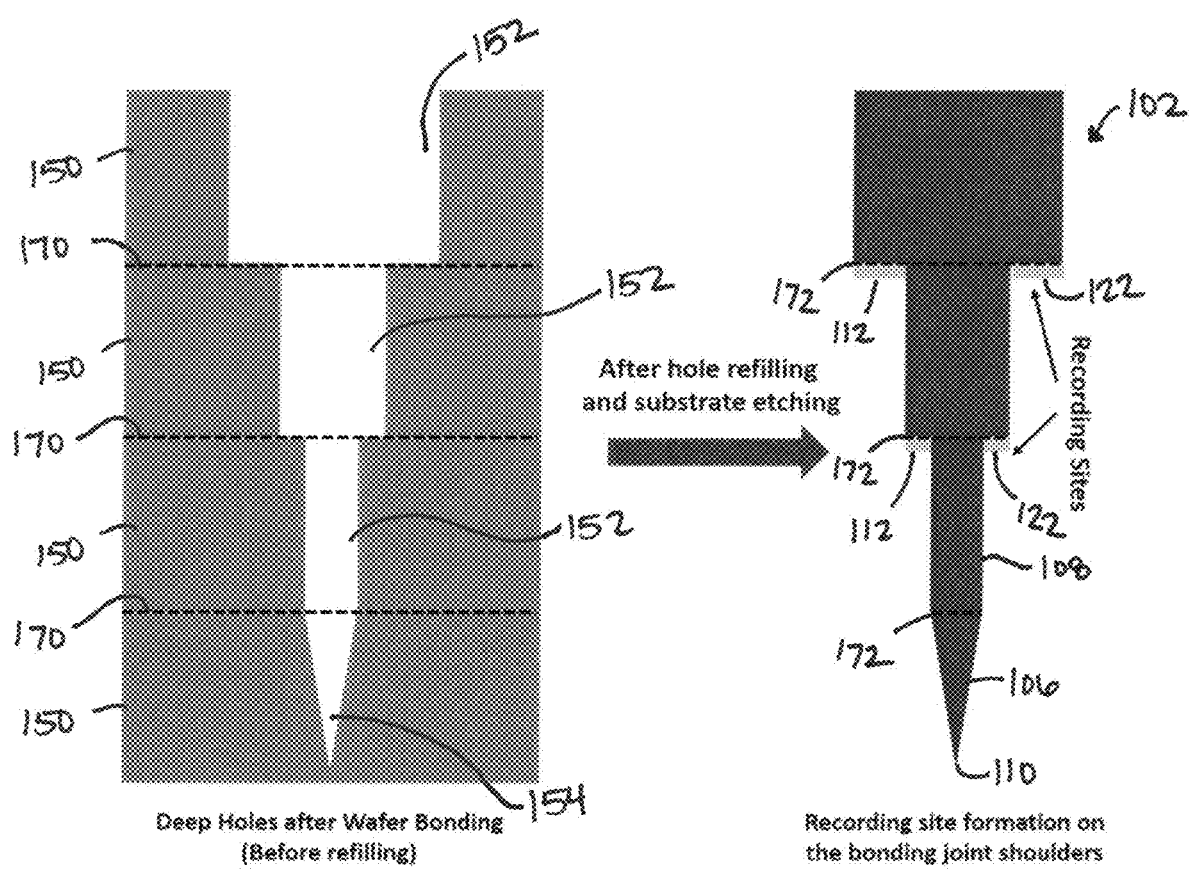
*FIG. 29A*  *FIG. 29B*

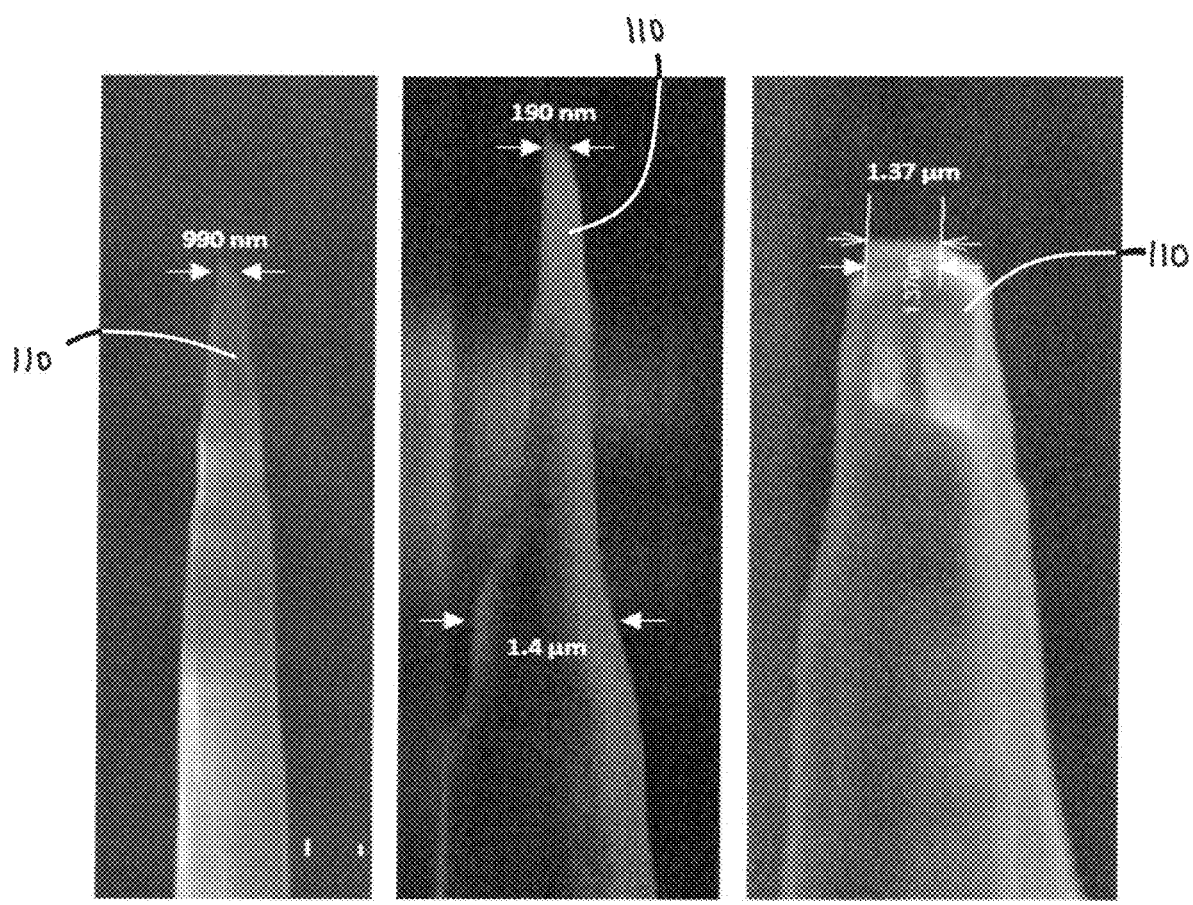
*FIG. 30A*  *FIG. 30B*  *FIG. 30C*

METHOD OF MANUFACTURING A PROBE ARRAY

CROSS-REFERENCE TO RELATED APPLICATIONS

This application claims the benefit of U.S. Provisional Application No. 62/688,800 filed Jun. 22, 2018, the entire contents of which is hereby incorporated by reference in its entirety.

TECHNICAL FIELD

This invention relates to electrode or probe arrays, and more particularly, to probe arrays comprising a plurality of neural probes.

BACKGROUND

A neural interface is a bidirectional transducer used to communicate with neurons either in the central nervous system (CNS) or nerves in the peripheral nervous system (PNS). This communication may be established through an interface site which can be realized by electrodes, waveguides and/or fluidic ports for electrical, optical and chemical recording and stimulation, respectively. Neural interface technologies are widely used to study the brain by mapping neural circuits using implanted probes in different regions of the brain. Neural recording and stimulation using microprobe arrays have been an essential part of decoding neural networks. Implantable probes with a myriad of shapes, designs, and materials have been widely used to study the brain by recording the electrical and chemical responses of neural structures and circuits. The ever-increasing need to map larger collections of neurons has pushed the scientific and engineering community to develop new technologies and designs capable of allowing this, but with limited success and progress.

The number of simultaneously recorded neurons has approximately doubled every seven years since the 1950s. The number of available sites in neural probes for simultaneous recording has been doubled almost at the same rate since the 1930s. Yet still, the number of available recording sites is lacking to obtain a more comprehensive neurological analysis, and the ability to study neural circuits and structures has been limited and contained by the lack of suitable multi-channel probes. This limitation is driven by the types of fabrication technologies and available designs and materials for making such probes. The need to increase the number of sites is motivated by the need to accurately map brain circuits, which can be improved by increasing the number of simultaneously recorded neurons in various parts of the brain. Moreover, high-density electrode arrays are required to obtain higher spatiotemporal resolution and better understanding of brain network functionalities.

Using no more than a few hundred small electrodes in the brain, people with paralysis have been able to control prosthetic arms for things like self-feeding and computer control. Reliable interfacing with the nervous system may be able to treat an even wider range of medical conditions, but because signals are mixed at the level of single cells, one must be able to access thousands or millions of individual neurons or nerve fibers to record from or control the system. Some efforts are being made toward arrays with tens of thousands of electrodes, but these probe systems have challenges. Systems with penetrating electrodes are limited in the number of electrodes and are difficult to properly package and integrate. Systems using surface electrodes have poor signal specificity. Accordingly, a need exists for technology capable of manufacturing high-density electrode arrays scalable to millions of electrodes with high spatiotemporal resolution. Further, extremely sharp and small electrodes (e.g., the size of capillaries) that fit through the interstitial spaces between cells with minimal damage are desirable. In addition, providing close-packed electrical, optical, and chemical reading/stimulating probes could provide neuroscientists great opportunities in studying neuronal interaction under various circumstances.

Traditionally, sites on a multi-site neural probe can be arranged in a number of ways, referred to as linear (1D or 1.5D), planar or areal (2D), and volumetric (3D). Not all of these different arrangements can be easily fabricated. Linear 1D probes provide a series of individual sites along the length of a shank. This simple structure has indeed been extremely useful for many years because it has allowed researchers to use these penetrating depth probes to study neural circuits in the cortex by allowing access to different neural regions. These linear 1D arrays are still extremely useful and utilized widely by the neuroscience community. One of the most advanced 1.5D probes (i.e., probes with many groups of a few sites distributed primarily along the probe shank) has ~1356 sites along a 8 mm long probe. 2D arrays consist of many sites distributed on multiple probe shanks to record from neurons along an imaginary plane formed by the sites. Many penetrating probe technologies offer multiple shanks. For example, 1000 electrodes on five parallel shanks has been reported. In such 2D probes, the recording plane is primarily perpendicular to the surface of the cortex (i.e., the recording plane is the same as the plane formed by the probe shanks). 2D probes can alternatively be formed by an array of probes whose tips form the recording sites, which form a recording plane. In this case, the recording plane is primarily parallel to the cortical surface, allowing recording from a single neural layer. The most well-known, and probably most widely-used, probe of this kind is the Utah Electrode Array (UEA), which is fabricated using planar microfabrication from silicon. 2D arrays have also been demonstrated with significant improved capabilities and with many more sites by bundling insulated microwires or fibers, or by assembling carbon fibers, each of which forms a recording site at the tip. Injectable macro-porous networks or recording sites formed on extremely thin and flexible layers of polymers have also been reported. These recording electrodes are formed in a 2D fashion on a polymer substrate, which is then rolled up and injected through a delivery needle. The rolled film opens up once in tissue and ostensibly forms a 2.5D arrays of recording sites. The location and exact distribution and shape of location of the sites is accordingly not controllable. The UEA, like the microwire or carbon bundles, is 3D in structure but primarily 2D in its recording ability. The slanted UEA allows recording from multiple neural layers with its recording plane angled to the cortical surface, and is referred to as a 2.5D probe. Most of these 1D and 2D probes exhibit excellent in-depth spatial resolution, however their poor areal coverage due to their large shank size or large shank-shank separation limits their use in applications which require large-scale recording within a specific depth of brain. In this case, probes with wider shanks or multiple parallel probes are needed to cover a larger area which both will result in more tissue damage and reduced chronic stability. Out-of-plane electrode arrays can potentially have sufficient planar (areal) coverage, however they have a poor depth coverage. These shortcomings, in terms of latitudinal and longitudinal spatial resolution, have hindered true three-dimensional neural studies with high spatial resolution.

3D recording arrays should be capable of recording from neurons distributed in a volume of tissue. Multiple sites are distributed along the length of several shanks, which are themselves distributed along an area of tissue. The distribution and layout of the shanks and the sites located along their length defines the volume from which recordings can be obtained. The Michigan group demonstrated one of the earliest 3D probes of this kind for both recording and stimulation. The 3D system consisted of 2D multi-shank silicon probes fabricated using planar microfabrication techniques and then assembled onto a platform with precisely arranged features to accommodate and align the 2D probes into the final 3D structure. A large-count 3D probe has also recently been demonstrated by stacking several individual planar multi-shank and multi-site silicon probes, instead of assembling them through a platform as the Michigan group did. The Michigan system also included electronics on individual probes or on the supporting platform for signal amplification and multiplexing to enable recording from all sites simultaneously. These two systems separated in time by almost 20 years represent true 3D recording probes. The structure of both of these probe arrays is also similar to the UEA, that is, the probes consist of many probes, with the difference being that the Michigan/Caltech electrodes can each support a linear array of recording sites, whereas the Utah electrodes could each support only one recording site at the tip of each probe.

Many different kinds of multi-channel probes are available today, utilizing different fabrication technologies. These fabrication technologies may be categorized into two broad classes. One utilizes assembly and manipulation of individual probes (such as carbon fibers or microwire bundles) to fabricate the final array structure. This approach could work well when making only a few complete systems, and where precision is not needed in either making the individual probes (e.g., control of dimension, tip shape, sharpness, etc.), or in controlling the features of the multi-probe array (e.g., minimum distance between probes, distribution pattern of probes). Although some of these aspects could be better controlled using mechanized tools, ultimately these systems are limited to at best a few thousand probes, and they may provide limited precision and control for applications that require such precision. The second approach relies on planar microfabrication technologies, such as those used for semiconductor electronics fabrication. This approach provides excellent control over device dimensions, material properties, and pattern and shapes on a two-dimensional plane. Anything that can be fabricated on a silicon wafer, can be fabricated with precision and extreme control and freedom over layout and shape. The main drawback of this approach is that anything that needs to have a third dimension and be thicker than ~0.5 mm (which is the thickness of a standard 4 inch diameter silicon wafer) cannot be fabricated in silicon. The UEA discussed above, is the only silicon 3D array not needing assembly following fabrication, however, it does not actually utilize any of the precision microfabrication techniques, which limits how small or compact and dense it can make a needle array.

SUMMARY

According to one embodiment, there is provided a method of manufacturing a probe array, comprising the steps of: etching a plurality of substrates to form a plurality of body segment channels; at least partially aligning the plurality of body segment channels in each substrate of the plurality of substrates to form a plurality of axial trenches; lining the plurality of axial trenches with a sacrificial layer; at least partially filling the lined axial trenches with one or more layers of probe material to form coated probes; separating the coated probes from the axial trenches; and etching the sacrificial layer on the coated probes.

In accordance with various embodiments, the method of manufacturing a probe array may have any one or more of the following steps or features, either singly or in any technically feasible combination:

- the lining step, the filling step, or both involve gas-phase depositing;
- the lining step, the filling step, or both involve metal electroplating;
- the lining step, the filling step, or both involve polymer molding;
- the number of body segment channels are not the same in one or more of the plurality of substrates such that at least some axial trenches have different axial trench lengths;
- one or more body segment channels have different diameters such that one or more axial trenches have a variable depth axial diameter;
- the etching step comprises aspect ratio dependent etching (ARDE) that involves a deep reactive ion etching (DRIE) lag effect that at least partially forms at least some body segment channels with a tapered end portion;
- the etching step comprises the steps of: isotropic etching of a backside of at least one substrate of the plurality of substrates; and through-substrate DRIE etching a tapered end portion;
- at least some of the body segment channels are at least partially overlapping to form one or more coated probes with multiple recording/stimulation sites;
- at least some of the body segment channels are connected by one or more connecting passageways to form one or more coated probes with multiple recording/stimulation sites;
- each substrate of the plurality of substrates has a thickness in a range of about 100-900 μm, and 2-20 substrates are at least partially aligned to create a plurality of axial trenches, each axial trench having an axial trench length of about 1-2 mm;
- each substrate of the plurality of substrates has a thickness of about 500 μm, and 4 substrates are at least partially aligned to create a plurality of axial trenches, each axial trench having an axial trench length of about 1.7 mm;
- the sacrificial layer is a cladding layer and the probe material is a waveguide having a higher refractive index than the cladding layer, and the probe array comprises a light source configured to transmit light through the waveguide;
- the filling step is performed to create a hollow core in one or more of the coated probes, and a tip end of the one or more coated probes is etched to form a microfluidic channel;
- bonding the plurality of aligned substrates before the lining step; and/or
- at least some of the body segment channels are grouped to form a probe cluster in the probe array.

According to another embodiment, there is provided a method of manufacturing a probe array, comprising the steps of: aspect ratio dependent etching (ARDE) a substrate to form a plurality of body segment channels; using a deep reactive ion etching (DRIE) lag effect to at least partially form a plurality of axial trenches that include a tapered end portion at each of the body segment channels; lining the plurality of axial trenches with a sacrificial layer; at least partially filling the lined axial trenches with one or more layers of probe material to form coated probes; separating the coated probes from the axial trenches; and etching the sacrificial layer on the coated probes.

According to another embodiment, there is provided a method of manufacturing a probe array, comprising the steps of: etching a substrate to form a plurality of axial trenches; lining the plurality of axial trenches with a sacrificial layer; at least partially filling the lined axial trenches with one or more layers of probe material to form coated probes; separating the coated probes from the axial trenches; and etching the sacrificial layer on the coated probes.

According to another embodiment, there is provided a method of manufacturing a probe array, comprising the steps of: preparing an electrode wafer and an interconnection wafer; bonding the electrode wafer and the interconnection wafer; forming a plurality of electrode tip portions in the electrode wafer; etching at least part of the electrode wafer to form a plurality of shank portions corresponding to the plurality of electrode tip portions, each shank portion and corresponding electrode tip portion comprising a probe; and electrically connecting each electrode tip portion to a proximal end of each corresponding shank portion.

In accordance with various embodiments, the method of manufacturing a probe array may have any one or more of the following steps or features, either singly or in any technically feasible combination:
- lining each probe with an insulation layer and etching at least part of the insulation layer to form a conductive tip end;
- metallizing the conductive tip end; and/or
- patterning a distal end of the interconnection wafer to form a contact pad for each probe.

According to another embodiment, there is provided a probe array, comprising: a substrate; and a plurality of probes attached to the substrate, each probe having a shank portion and an electrode tip portion, the shank portion comprising a plurality of alignment junction portions spaced along a length of the shank portion.

In accordance with various embodiments, the probe array may have any one or more of the following features, either singly or in any technically feasible combination:
- each electrode tip portion includes a tip end, wherein the tip ends comprise a variable depth insertion topography;
- the variable depth insertion topography has a shape that conforms to one or more undulations in a brain structure;
- the electrode tip portion extends from a tip end to a proximal facing shoulder at a proximal end of the shank portion and the proximal facing shoulder of each probe includes a recording/stimulation site;
- the probe array further comprises a light source and at least one probe in the array has a waveguide; and/or
- the at least one probe includes a microfluidic channel.

According to another embodiment, there is provided a probe array, comprising: a substrate; and a plurality of probes attached to the substrate, each probe having a shank portion and an electrode tip portion, the electrode tip portion having a tip end, a proximal facing shoulder at a proximal end of the shank portion, and a tapered wall extending between the tip end and the proximal facing shoulder, wherein the proximal facing shoulder includes a recording/stimulation site.

BRIEF DESCRIPTION OF THE DRAWINGS

Preferred exemplary embodiments will hereinafter be described in conjunction with the appended drawings, wherein like designations denote like elements, and wherein:

FIGS. 9A-9C illustrate various embodiments of multimodal probes for a probe array, with FIG. 9A showing a combined electrophysiology and optical probe, FIG. 9B showing a combined electrophysiology and chemical delivery probe, and FIG. 9C showing a combined electrophysiology, optical, and chemical delivery probe;

FIGS. 10A-10E illustrate steps of one embodiment of manufacturing a probe for a probe array;

FIGS. 12A-12E illustrate another embodiment of manufacturing a probe for a probe array;

FIGS. 16A-16E are SEM images showing recording or stimulation sites of a probe for a probe array;

FIGS. 17A-17E illustrate a method of forming recording or stimulation sites, such as the recording or stimulation sites shown in FIGS. 16A-16E;

FIGS. 19A-19F illustrate another embodiment of a method of manufacturing a probe array;

FIG. 20 illustrates an embodiment of a probe;

FIG. 21 is a cross-section of the probe of FIG. 20;

FIGS. 22A-22C illustrate a method of manufacturing the probe of FIGS. 20 and 21;

FIGS. 25A and 25B illustrate a body segment channel for forming a probe, and an illustration of the formed probe, respectively;

FIGS. 29A and 29B illustrate an axial trench for forming a probe, and an illustration of the formed probe, respectively; and FIGS. 30A-30C illustrate various embodiments of probes having different probe tip ends.

DESCRIPTION OF THE ILLUSTRATED EMBODIMENTS

Figure 1A:
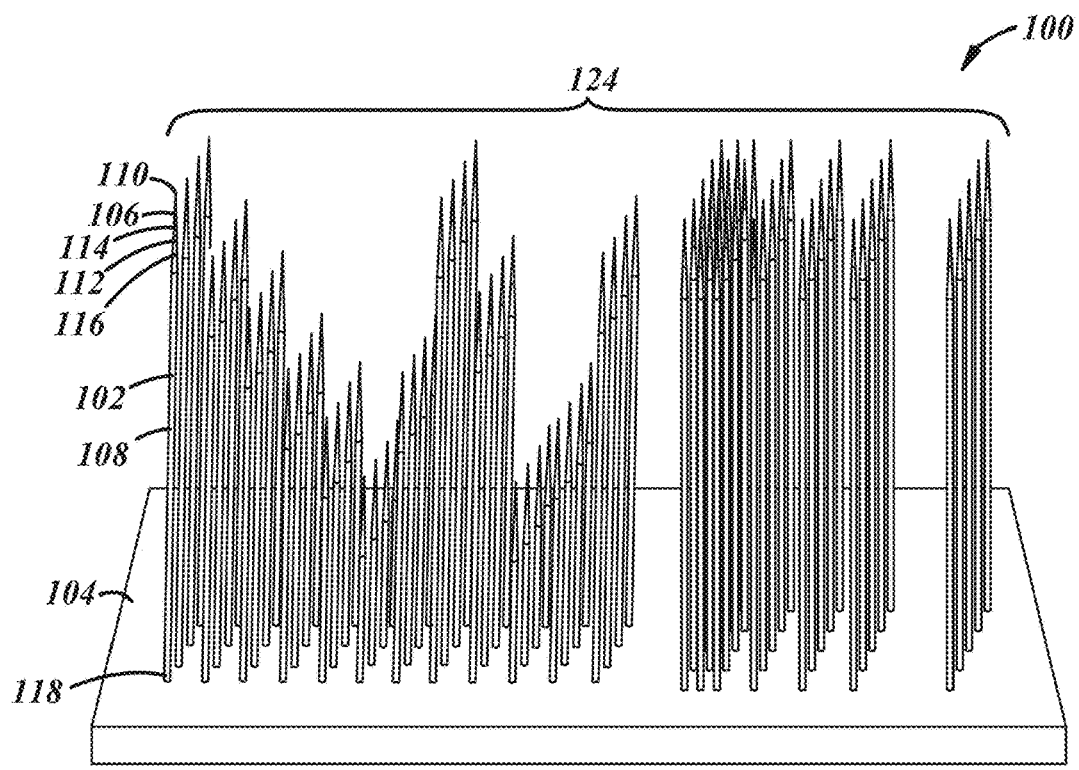
FIGS. 1A-1D illustrate a probe array according to one embodiment, with FIG. 1A showing the overall probe array and FIGS. 1B-1D showing different cross-section views of the probe array in FIG. 1A.

As described herein, a method of manufacturing a probe array allows for the creation of a customizable, three-dimensional, high-density, high-electrode-count probe arrays scalable to thousands and even millions of individual probes. These 3D, high-density, high-electrode-count neural micro-probe arrays can potentially give neuroscientists huge opportunities in restoring vision, hearing, full-body movements and memory. In some embodiments, deep reactive ion etched (DRIE) ultra-high aspect-ratio holes are etched in silicon and then refilled with multiple films to form thousands of individual probes with metal recording and/or stimulation sites/tips making up the "sea-of-electrodes" array (SEA). World-record density of 400 electrodes/mm$^2$ in a 5184-probe array is achieved; however, other probe densities and probe counts are certainly possible. The probes in some embodiments are millimeter-long, 10-20 μm wide at the base, and <1 μm at the tip. DRIE and its lag effect may be used to control tip sharpness and electrode length by only changing the hole diameter, thus allowing narrow, long, and dense needles to be formed side-by-side in a single array. Moreover, arbitrary distribution of probes with different lengths, pitches, and diameters is demonstrated. This allows for easy array implantation into the brain's convoluted surface for high spatiotemporal resolution, and access to neurons in various regions of the brain with reduced tissue damage. Furthermore, the described fabrication approaches allow each probe to have a recording/stimulating site near its tip, a waveguide within its core for optical transmission, and/or a microfluidic channel that could be utilized for administering drugs and/or constructing chemical sensors. Multimodal probe arrays may also be manufactured, wherein some probes have a recording/stimulating site, other probes have a waveguide, and yet other probes have a microfluidic channel, to cite a few possibilities.

Probe Array—

FIGS. 1A-1D and 2 illustrate embodiments of a probe array 100. Each probe array 100 includes a plurality of probes 102 attached to a substrate 104 (only one probe 102 and its respective parts are labeled in each of the figures for clarity purposes). The probe array 100 may be manufactured with a very dense and high-count array of probes 102. In this embodiment, the probes 102 are fine and slender insulated silicon needles with variable length and width, a tapered cross-sectional shape along their length, and sharp tips. Each probe 102 includes an electrode tip portion 106 and a shank portion 108. The electrode tip portion 106 in this embodiment includes a tip end 110, a proximal facing shoulder 112, and a tapered wall 114 therebetween. The shank portion 108 includes a shank portion proximal end 116 at the proximal facing shoulder 112 and a distal end 118 that is attached to the substrate 104. As will be detailed further below, one or more probes 102 of the probe array 100 may include one or more recording/stimulation sites, and/or a waveguide for light transmission, and/or a microfluidic channel, which may or may not be instrumented for chemical sensing.

Figure 1B:
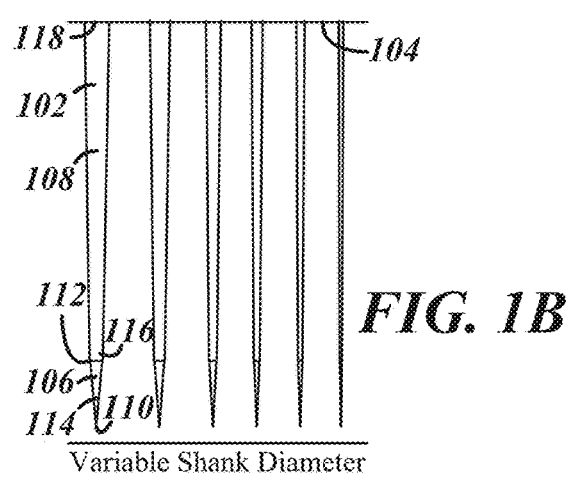
Figure 1D:
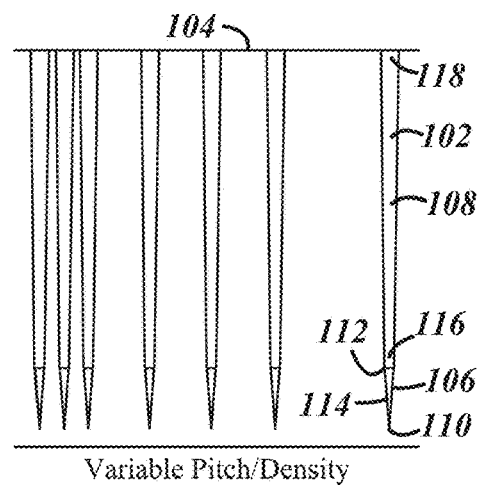
Figure 1C:
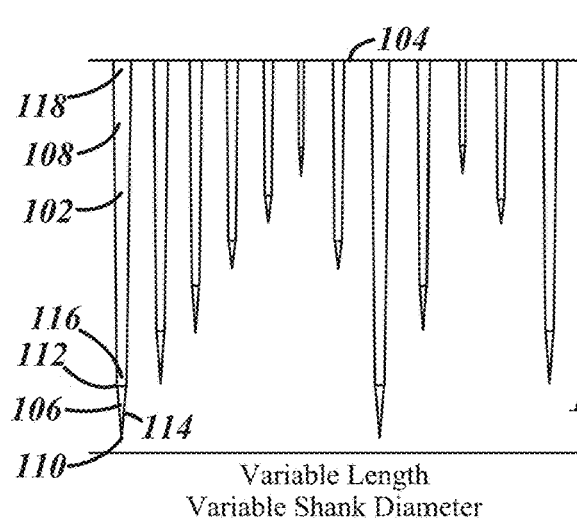

FIG. 1B shows that each probe 102 may have different diameters (both at the electrode tip portion 106 and the shank portion 108). Having different diameters can help in engineering a particular or desired stiffness of each probe 102. Electrode tip portions 106 and/or shank portions 108 may be as small as a few microns in diameter. A tradeoff between stiffness and flexibility, which may be at least partly correlated with the diameter, can be tailored for various desired applications. FIG. 1C illustrates probes 102 having different lengths, and still residing side-by-side. Probes 102 as tall as tens of microns to tens of millimeters can be fabricated as needed in many applications. FIG. 1D illustrates that it is possible for the probes 102 to have variable pitch/density, with probes capable of being spaced as close as 10 μm. The conical shape of the tip and/or shank portions 106, 108 may be obtained through particular manufacturing processes, including in one embodiment detailed further below, a deep reactive ion etching (DRIE) lag effect. DRIE etch rate is inversely proportional to the aspect ratio of the channel/trench, in other words, channels/trenches with higher ratio of depth to width are etched slower. The variable etch rate at different depths will result in the conical shape of the shank portion 108, producing a sharp tip portion 106 which improves probe insertion into the tissue and can reduce the tissue damage and possible subsequent adverse tissue reactions. FIG. 1A illustrates a probe array with a distribution of probes having various lengths, diameters, and pitches/densities across the array.

Figure 2:
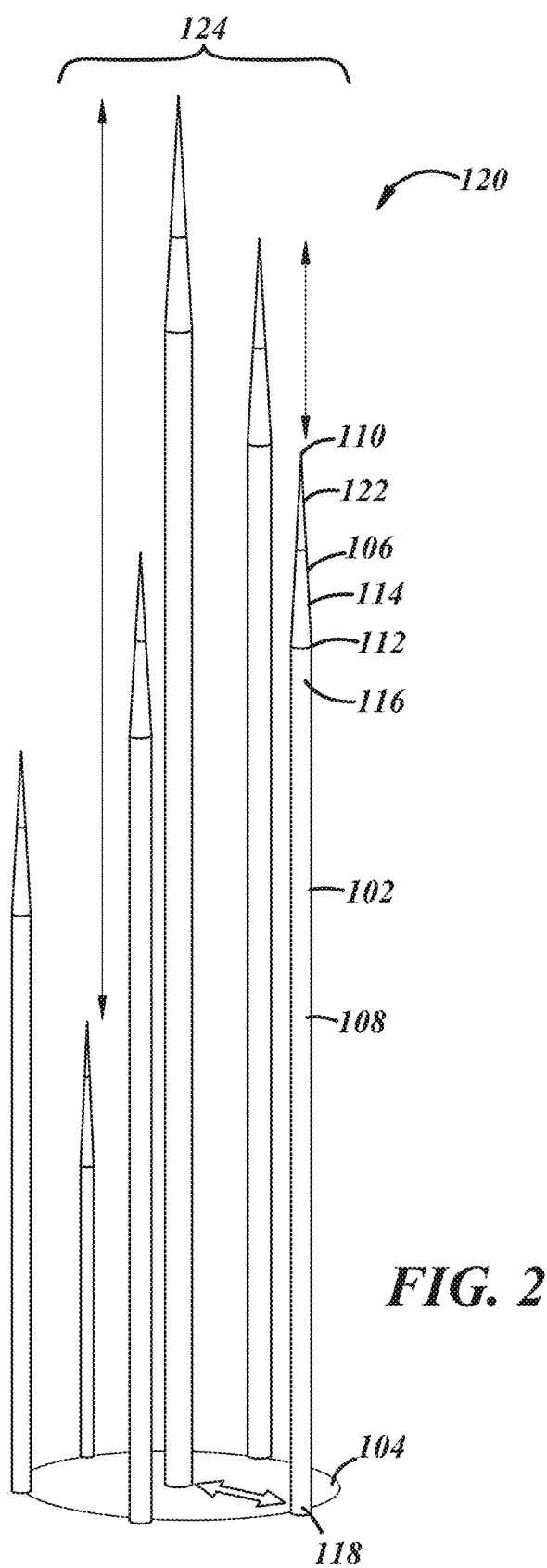
FIG. 2 shows another embodiment of a probe array.

FIG. 2 illustrates a probe cluster 120, which may be used in some embodiments, like a tetrode, to monitor neural activity in-depth within the same column of tissue. A probe array 100 may be comprised of several distinct probe clusters 120. FIG. 2 also more clearly shows a recording/stimulation site 122, which is located at a metallized tip end 110. References herein to a recording/stimulation site may be a site capable of recording only, stimulation only, or both recording and stimulation. The tip ends 110 at different heights may form a variable depth insertion topography 124. The variable depth insertion topography 124 may have a shape that conforms to one or more undulations in a brain structure, as will be detailed further below. By reducing the distance between the individual probes in the cluster 120, one can obtain a multi-site per probe shank structure wherein recording and/or stimulation from various tissue layers using an individual cluster probe 124 is possible.

Figure 3:
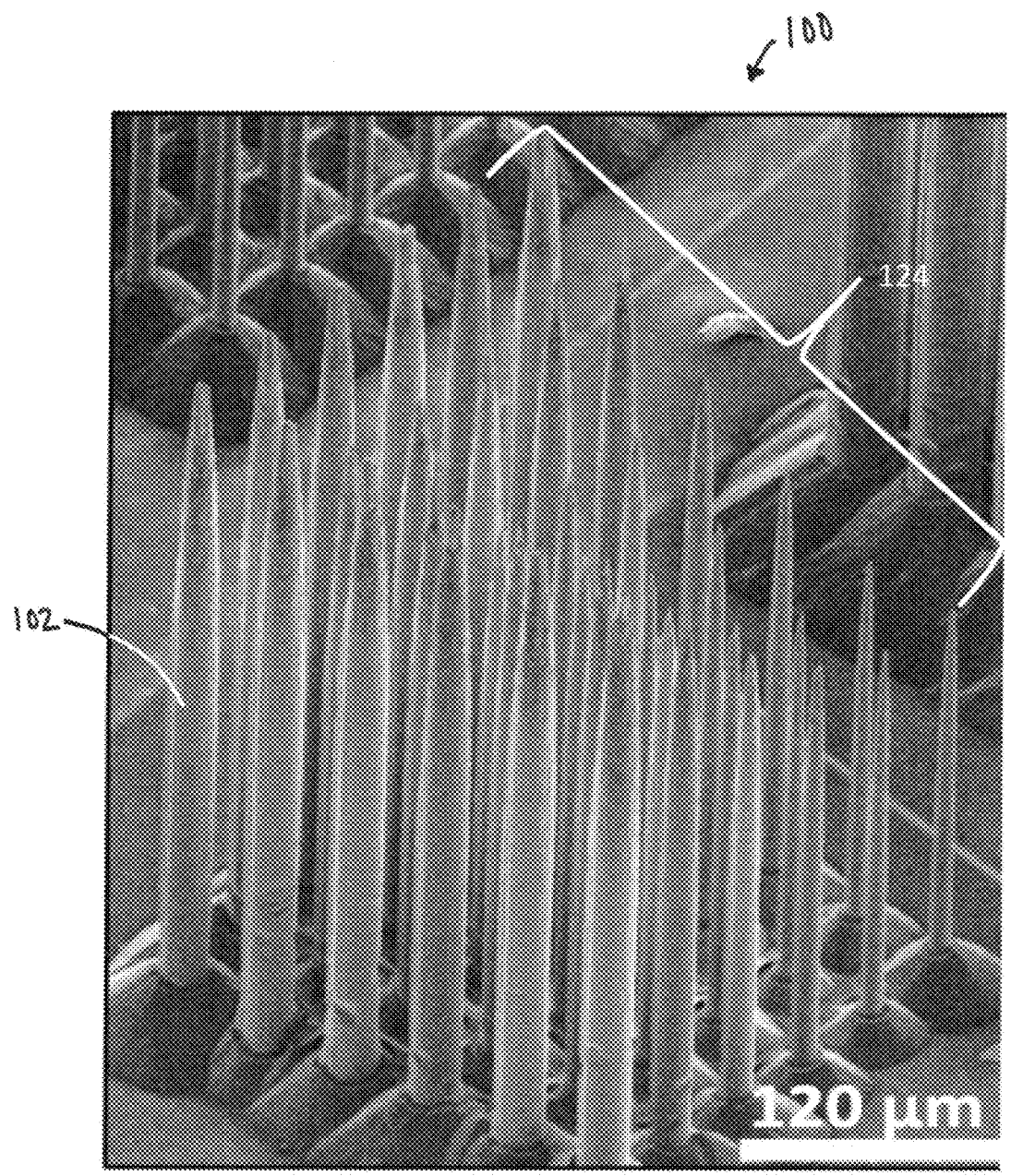
FIG. 3 is a scanning electron microscope (SEM) image of a probe array.
Figure 4:
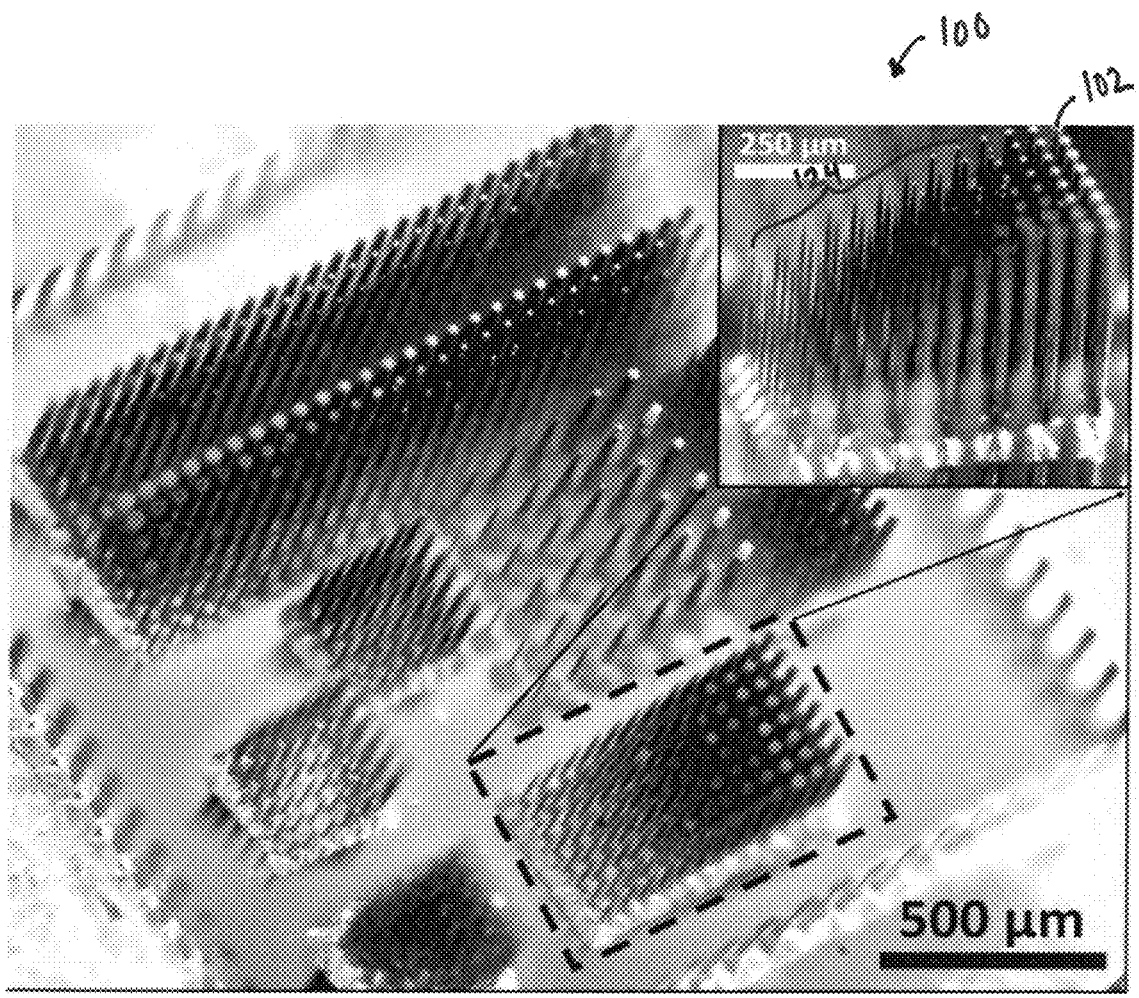
FIG. 4 is an optical image of a probe array.

FIGS. 3 and 4 illustrate other embodiments of a probe array 100 having a variable depth insertion topography 124. FIG. 3 is an SEM image of fabricated side-by-side probes 102 with varying length and diameter. FIG. 4 is an optical image of an array 100 with a distribution of probes 102 with various lengths, shank diameters, and pitches. The arrays 100 and variable depth insertion topographies 124 allow for recording and stimulation of a larger number of neurons in the implanted tissue volume using a minimal number of electrodes, resulting in less tissue damage and improved chronic stability. Further, successful recording and manipulation of neurons across multiple spatial latitudinal and longitudinal planes is possible with high spatial resolution. Studies have shown that the probe size can play an important role in determining tissue damage and chronic stability of the implanted array 100. Any desired distribution of probes with various lengths, shank diameters and concentrations across the array 100 can be obtained. Employing a variable depth insertion topography 124 can enable true 3D access of neurons with extremely high spatial resolution, with more successful implantation into the brain convoluted surface and simultaneous recording/stimulation of neurons in various depths of tissue.

Figure 5:
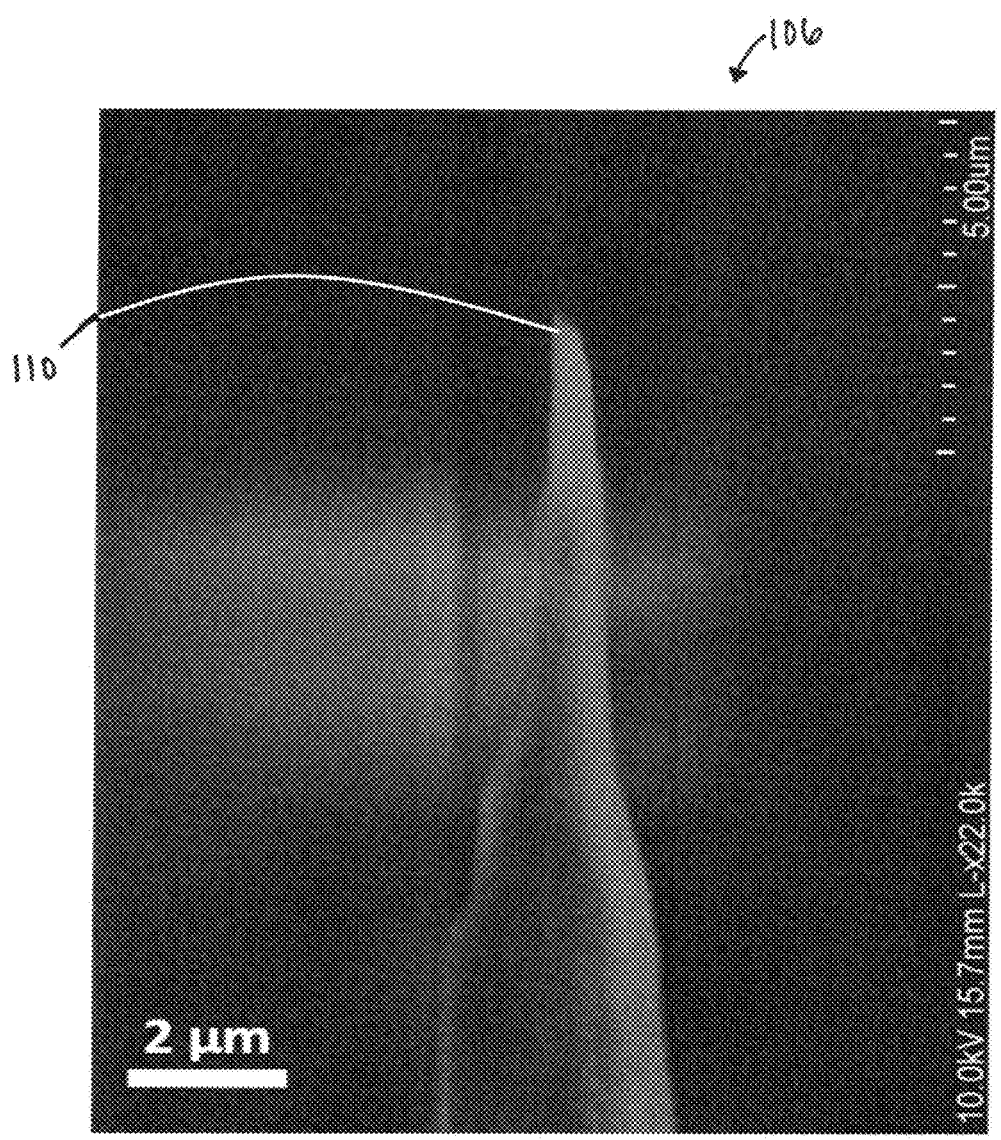
FIG. 5 is an SEM image of an electrode tip portion of a probe from a probe array.
Figure 6:
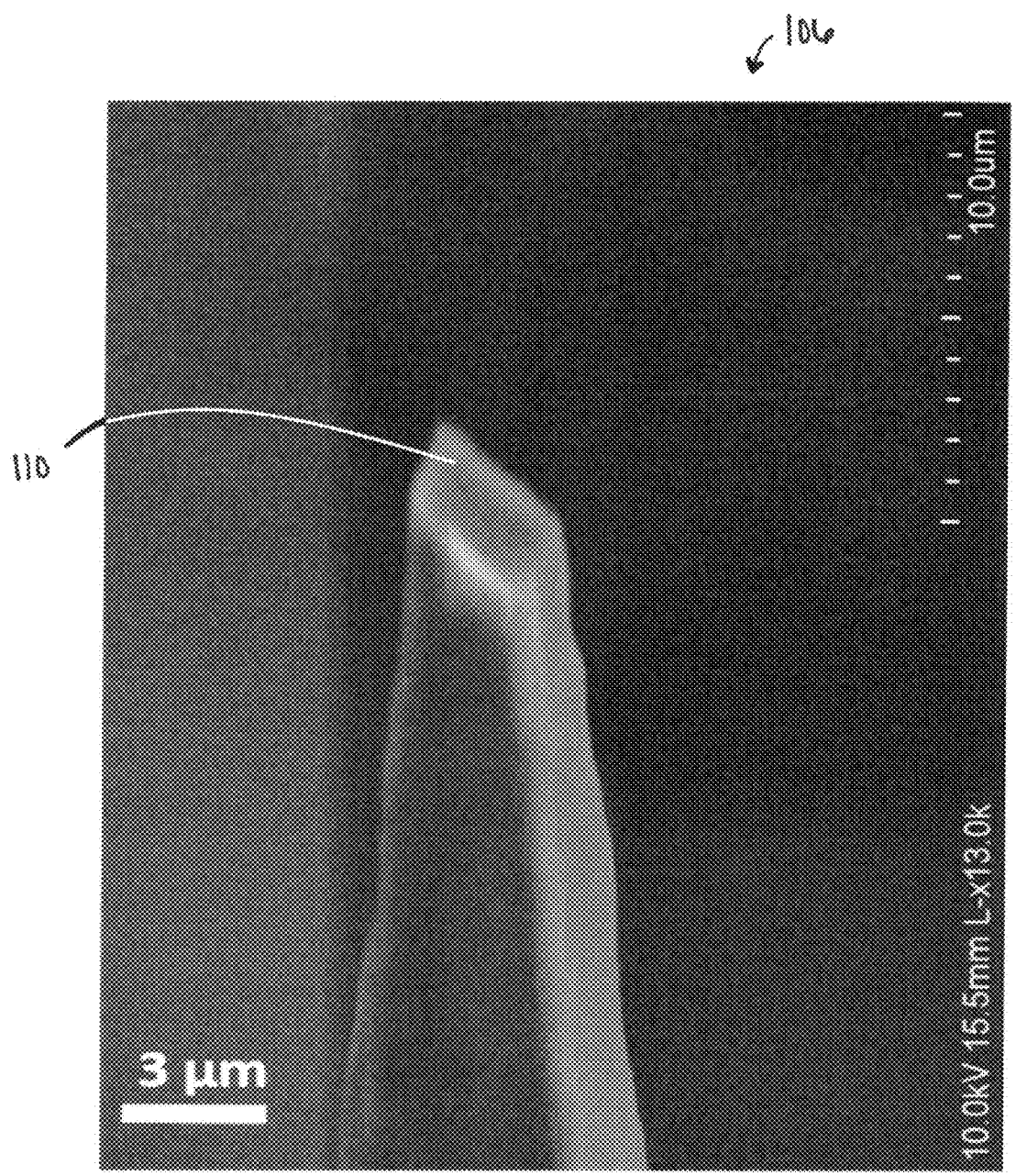
FIG. 6 is an SEM image of an electrode tip portion of a probe from a probe array.

FIGS. 5 and 6 are SEM images of submicron sized electrode tip portions 106. FIG. 5 is an electrode tip portion 106 from a shank that is about 10 µm thick, and FIG. 6 is an electrode tip portion 106 from a shank that is about 20 µm thick. Sharp tips 110 and small probe shank size reduces the tissue damage during the implantation and post-implantation, improves the chronic stability and increases the array density.

Figure 7:
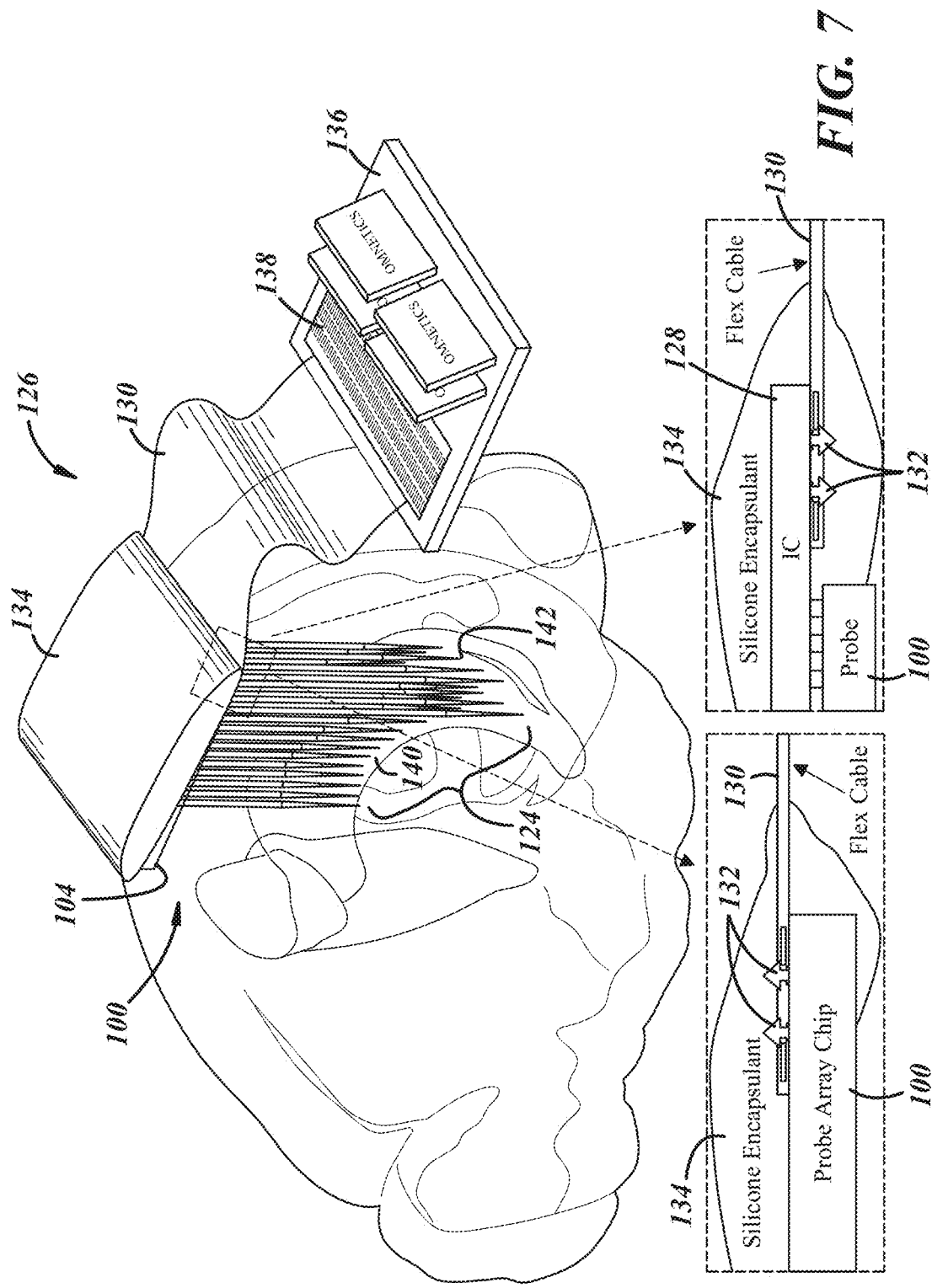
FIG. 7 illustrates an implanted probe array in a rodent brain.

FIG. 7 shows all of the components of a probe array microsystem 126 according to one embodiment, including the probe array 100, an integrated circuit (IC) chip 128 for site selection and multiplexing if needed, a flexible ribbon cable 130, and connectors 132. As shown, in one embodiment, the probe array 100 may have an integrated IC chip (or no IC chip), or in another embodiment, the probe array 100 has a separate IC chip 128. The array 100 is either attached to the flexible cable 130 using rivet bonding, or to the IC chip 128 using flip-chip solder bonding. The junction may be encapsulated using a silicone encapsulant 134. Silicone for the encapsulant 134 can provide insulation for many months. The cable 130 is attached to a printed circuit board (PCB) 136 using supporting connections 138. The PCB 136 may or may not be attached to the rat skull (not shown). The flexible cables 130 may be, in one embodiment, polyimide or parylene cables. In a particular embodiment, the cables 130 will be about 10 µm thick, a few millimeters wide, and a few centimeters long to support interconnection lines with a 10 µm pitch (5 µm wide and 5 µm spacing).

The cables 130 can be attached to the array substrate 104 that supports bonding pads on its top surface through the use of rivet bonding. As shown on the left, openings in the cable 130 are aligned with contact pads 132 on the array and then gold bumps are placed on the openings using a wire bonder to form the rivet bonds. As shown on the right, it is also possible to directly attach the flexible cable 130 to an IC chip 128 for amplification, multiplexing, and site selection. The IC chip 128 can be flip chip mounted to the probe array 100 using solder bonding. The other end of the flexible cable 130 is then attached using wire or rivet bonding to the PCB 136 that supports a number of Omnetics™ connectors in this embodiment. Alternatively, because of the large number of bonds, the ribbon cable 130 could be bonded to the PCB 136 using anisotropic conductive film (ACF) technology. The integration of the microsystem 126 can be completed by the Omnetics™ connectors to the PCB 136. The count of the Omnetics™ connector depends on the number of channels that the array 100 provides for electrical recordings.

FIG. 7 also more clearly illustrates one of the advantages of the variable depth insertion topography 124. In this embodiment, the variable depth insertion topography 124 has a hippocampal conformational pattern or shape which conforms to undulations 140, 142 in the rat hippocampus while only two undulations are labeled in the figure, those skilled in the art recognize that the hippocampus and other brain structures often have many undulations. This allows for successful recording and stimulation of hippocampal neurons across multiple spatial latitudinal and longitudinal planes in the brain while maintaining high spatial resolution.

Figure 8:
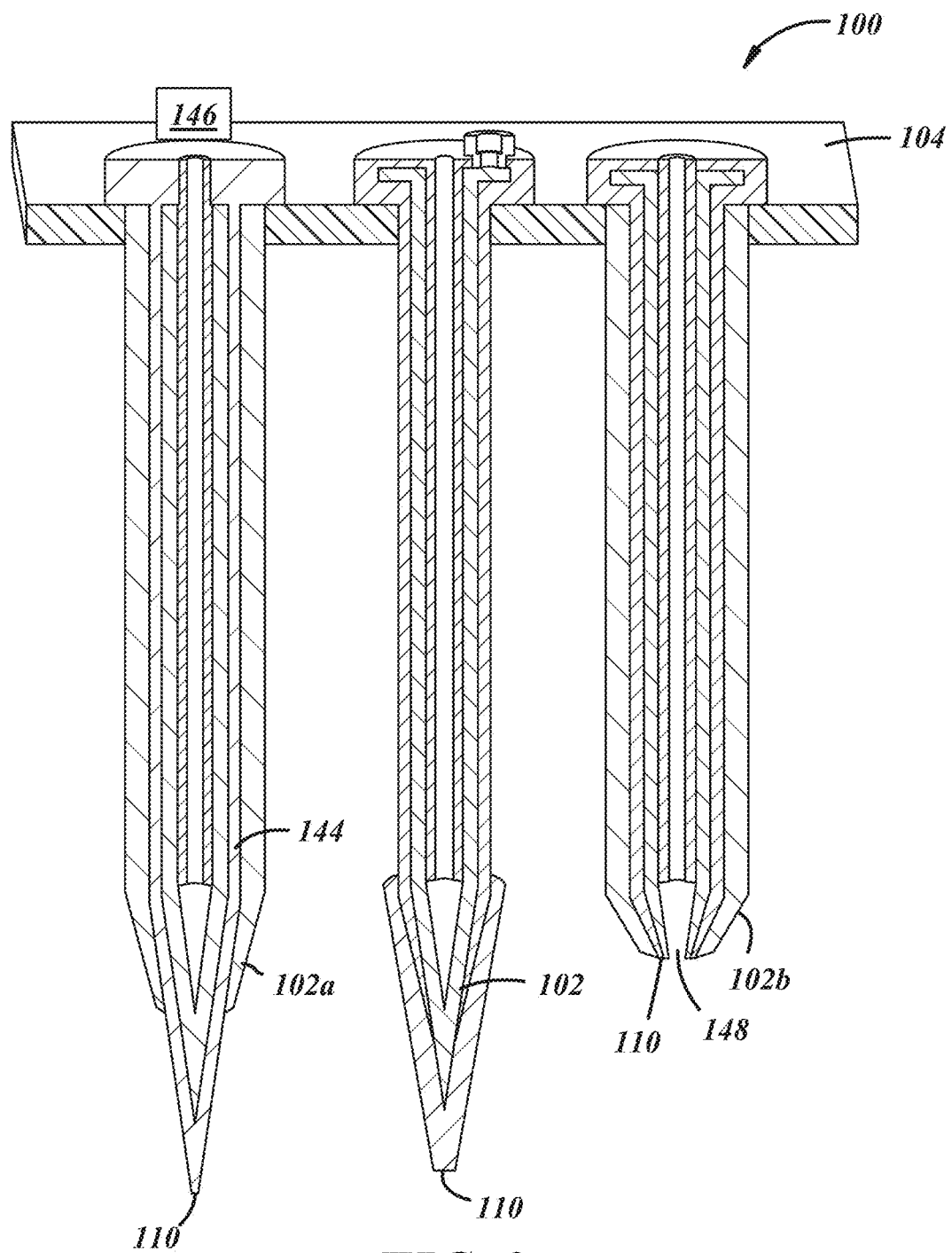
FIG. 8 illustrates an embodiment of a multimodal probe array.

FIG. 8 illustrates a multimodal probe array 100. This embodiment of a probe array 100 includes three types of probes 102: an electrophysiology probe 102 (e.g., a recording/stimulation probe), an optical probe 102a, and a chemical/drug delivery probe 102b. Optical interaction with neurons is advantageous, as it allows for the study of neurons that have been genetically modified to demonstrate light-sensitive behaviors. Thus, it is advantageous, in some embodiments, to guide light to neurons in cellular and subcellular resolution by means of the probe 102a having a waveguide 144 to direct light from a light source 146 to the tip end 110. Drug delivery and chemical stimulation of the neurons may also be advantageous for pharmaceutical drugs investigation and also in optogenetics. Thus, the neural probe 102b includes an integrated microfluidic channel 148. A microfluidic channel 148 can be easily integrated to the existing design by forming an opening at the tip end 110. As will be detailed further with respect to the manufacturing method, for the optical probe 102a, hole diameters should be chosen in a way that holes get fully refilled after a first dielectric (O—N—O) layer which will work as the optical waveguide 144. Chemical/drug delivery probes 102b can be obtained using holes with larger diameters to ensure the formation of the microfluidic channel 148 inside the probe, later an opening can be formed at the tip end by a maskless selective reactive ion etching (RIE) of the probe tip.

FIGS. 9A-9C illustrate various embodiments of multimodal probes 102. FIG. 9A shows a probe 102c that includes electrophysiologic capability via the recording/stimulation site 122 and optical capability from the waveguide 144 which can direct light from light source 146 to the tip end 110. FIG. 9B shows a probe 102d that includes electrophysiologic capability via the recording/stimulation site 122 and chemical or drug deliverable capability via the microchannel 148 at the tip end 110. FIG. 9C shows a probe 102e with all three: electrophysiologic capability via the recording/stimulation site 122, optical capability from the waveguide 144 which can direct light from light source 146 to the tip end 110, and chemical or drug deliverable capability via the microchannel 148 at the tip end 110. These probe embodiments include multiple functionalities to obtain electrophysiological recording and chemical sensing from the electrically, optically, and/or chemically stimulated neurons. This can improve the spatial resolution of neural stimulation and recording.

Manufacture—

Various fabrication technologies may be used in the manufacture of the probe arrays 100. The manufacturing methods below are scalable and capable of forming 3D arrays with high-density, high-electrode-count neural probes 102 made from silicon, in one embodiment, although another operable material may be used. To overcome the shortcomings and issues of previously reported arrays, a manufacturing method based on refilling deep ultra-high aspect-ratio holes in a silicon substrate or wafer with deposited layers, followed by etching away the support wafer to separate and leave thousands and eventually millions of probes 102, is disclosed herein.

FIGS. 10A-10E illustrate one embodiment of a method of manufacturing a probe 102. This method is scalable to a probe array 100 having many probes (e.g., the wafers will have multiple axial trenches, as detailed further below), but for clarity purposes, FIGS. 10A-10E illustrate only one probe 102. In this embodiment, a wafer or substrate 150 is etched using deep reactive ion etching (DRIE) aspect ratio dependent etching (ARDE) that involves a DRIE lag effect to form a body segment channel 152 with a tapered end portion 154. The substrate or wafer 150 may ultimately form the substrate 104 of the probe array, although in some embodiments, the substrate 104 of the probe array may not be formed by the substrate or wafer 150. The body segment channel 152 and tapered end portion 154 form an axial trench 156. The term "axial trench" may include a hole, recess, channel, cavity, etc., formed in the substrate 150. The axial trench 156 in this embodiment has a diameter of less than 25 μm and can produce a probe 102 having a sharp tip end 110. The length L of the axial trench 156 in this embodiment is about 500 μm. The shape of the trench 156 can be any operable shape, such as round, square, or rectangular, to cite a few examples.

FIGS. 10B-10E illustrate refilled axial trenches with multiple low pressure chemical vapor deposited (LPCVD) films. However, as will be detailed below, other lining and/or filling techniques are possible. With reference to FIG. 10B, first, the axial trenches 156 are lined with a sacrificial layer 158, which in one embodiment, is a sacrificial polysilicon LPCVD film layer of a few microns used to reduce the shank thickness. Second, an outer insulator layer 160 is deposited using LPCVD, which in this embodiment is an oxide-nitride-oxide (ONO) insulator layer. FIGS. 10C and 10E show a conductive core layer 162 and inner insulator layer 164, which in this embodiment, is n-type, highly doped polysilicon and ONO, respectively, deposited using LPCVD. The outer insulator layer 160, the conductive core layer 162, and/or the inner insulator layer 164 may constitute probe material layers which form the coated probes 102. The ONO insulator layers 160, 164 are used for electrical insulation and protection of the n-type polysilicon layer 162 during subsequent wet etching of the silicon substrate 150 that is needed (in this embodiment) to reveal the probes 102.

FIG. 10C also illustrates formation of a contact pad 166, which may be patterned metal, such as chromium and gold, on top of the wafer 150 to electrically access the conductive core layer 162. To provide electrical access to the polysilicon conductive core layer 162, the top dielectric ONO layer 164 may be selectively removed at a via 168. FIG. 10D illustrates separation of the probe 102 from the axial trench 156, which may be accomplished by dissolving the substrate wafer 150 by etching with ethylenediamine pyrocatechol (EDP), leaving behind instrumented and insulator-coated probes 102. This step may also etch the sacrificial layer 158. RIE etching, or more particularly, direction-dependent RIE, of the outer insulator layer 160 at the tip end 110 exposes the conductive core layer 162. FIG. 10E illustrates metallization of the tip end 110. A metal, such as chromium and/or gold, to cite two examples, may be used to form ohmic contact and help obtain proper impedance required for electrophysiological recording.

The diameter of the shank portion 108 is determined by the body segment channel size of the axial trench 156 in the layout and also the thickness of the sacrificial layer 158. The minimum body segment channel size is determined by DRIE limitations, since the probe length needs to be at least few hundred micrometers to be applicable, therefore, the sacrificial layer 158 can be used for thinning the shank. A thicker sacrificial layer 158 will result in thinner shanks. Dissolvable biocompatible materials can also be used as the sacrificial layer, this includes biodissolvable materials like starch, porous silicon, etc. Small shank size helps facilitate array insertion and chronic stability. To obtain chronic stability of a neural interface, minimal glial scarring is required which can be prevented by using subcellular scale shank size. Smaller shanks can also contribute to achieve higher density by reducing the pitch size.

Figure 11E:
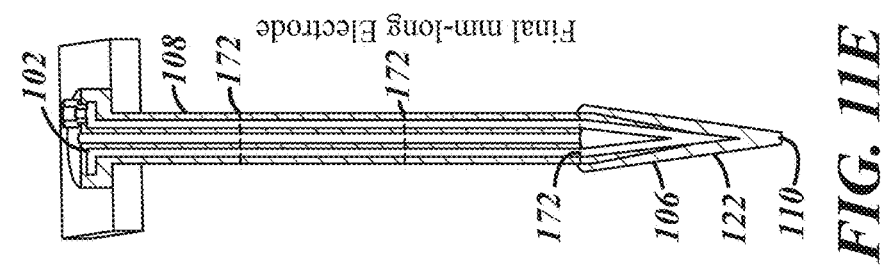
FIGS. 11A-11E illustrate steps of one embodiment of manufacturing a probe for a probe array with customizable probe lengths.
Figure 11D:
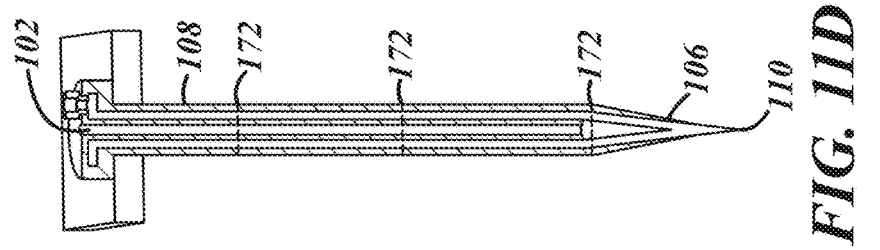
Figure 11C:
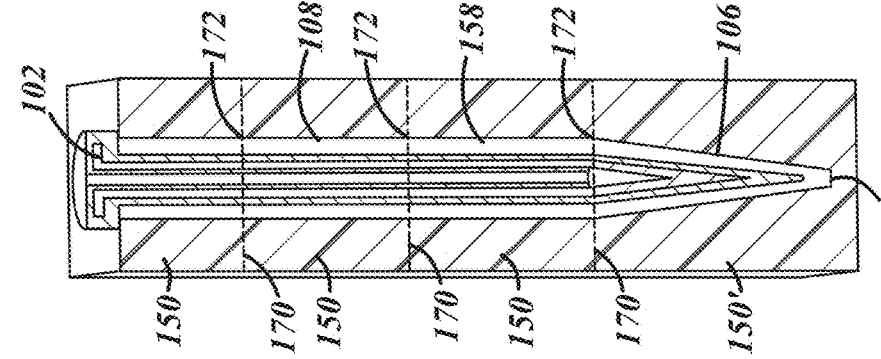
Figure 11B:
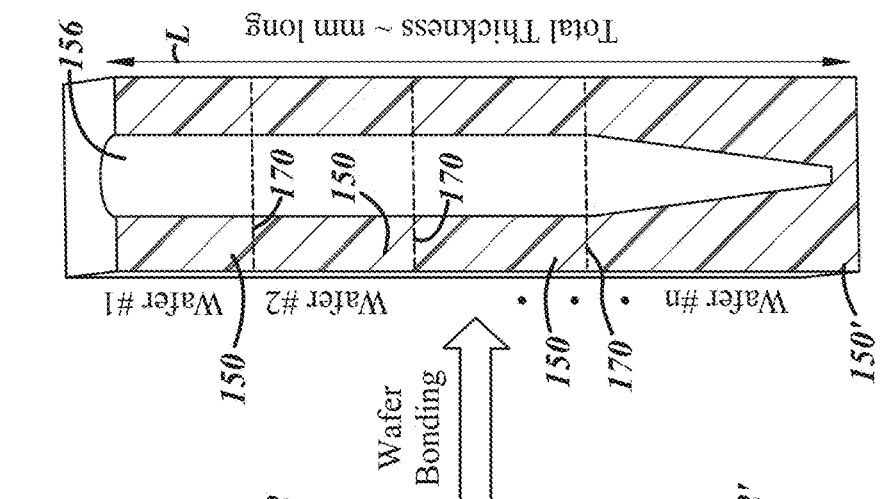
Figure 11A:
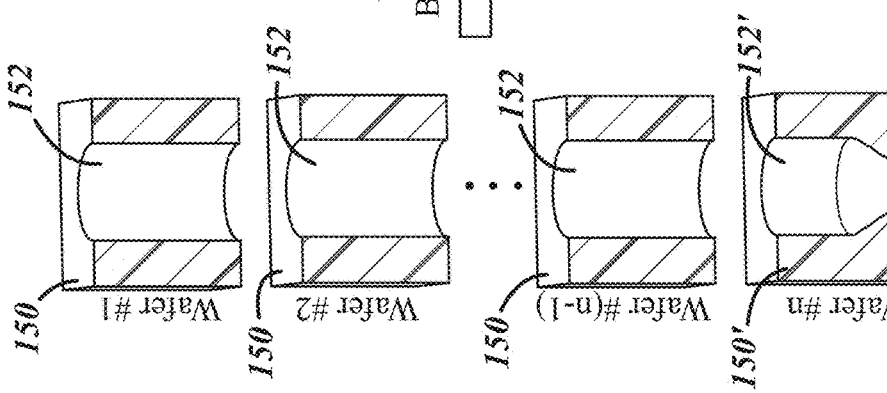

FIGS. 11A-11E illustrate another embodiment of a method of manufacturing a probe 102. As with FIGS. 10A-10E, this method is scalable to a probe array 100 having many probes 102 (e.g., the substrate or wafer 150 will have multiple axial trenches 156, as detailed further below), but for clarity purposes, FIGS. 11A-11E illustrate only one probe 102. FIG. 11A illustrates a plurality of etched wafers 150. Multiple separate substrates 150 are prepared with through-wafer etched body segment channels using a ultra-deep high-aspect-ratio ramped DRIE recipe or any other etching techniques. The wafer 150' is etched using a custom DRIE recipe that imparts a DRIE lag effect to form a tapered end portion at the bottom of the body segment channel 152'. The DRIE lag effect can help form the probe tip 110 shape and sharpness.

In FIG. 11B, the wafers 150, 150' are at least partially aligned and joined to form a mm-deep axial trench 156. Accordingly, alignment junction regions 170 form between the aligned and joined wafers 150, 150'. At each alignment junction region 170, a corresponding alignment junction portion 172 may form in the probe 102 at the end of the electrode tip portion 106 and along the length of the shank portion 108. This alignment junction portion 172 may have a slightly stepped configuration that coincides with the alignment junction regions 170 in the axial trench 156. The axial trench 156 has a shape that generally corresponds to the shape of the probe 102, and in this embodiment, the axial trench 156 has a length L of about 1 mm. Deep brain recording/stimulation applications require probes with lengths of 1 to 10 mm. Accordingly, this method can produce long enough probes for such deep brain recording/stimulation (e.g., more wafers 150 or thicker wafers 150 may be employed to increase the length of the axial trench 156). FIGS. 11C-11E illustrate various lining, filling, separating, and etching steps that may vary depending on the desired attributes of the manufactured probe array 100. These steps generally coincide with FIGS. 10C-10E described above. The sacrificial layer 158 can reduce the final probe shank diameter and can also fill the undesired gaps and voids formed during bonding of the substrates as shown in FIG. 11B.

FIGS. 12A-E illustrate another embodiment of refilling the axial trenches 156, which may be used in conjunction with either of the methods disclosed in FIGS. 10A-10E and 11A-11E. In this embodiment, electroplating is used to form the probes 102 instead of depositing all of the layers with LPCVD. In this embodiment, as shown in FIG. 12A, an initial conductive sacrificial layer 158 (e.g., n-type polysilicon) is deposited with LPCVD or another method in the axial trench 156 of a substrate or wafer 150 to be used for the following seedless electroplating. FIG. 12B shows a conductive core layer 162 being electroplated which then forms a metallic probe body as shown in FIG. 12C. The silicon wafer 150 and conductive sacrificial layer 158 are etched in EDP in FIG. 12D. Finally, in FIG. 12E, a parylene outer insulator layer 160 is then deposited, and the tip end 110 is exposed, using, for example, $O_2$ plasma etching, which forms a recording/stimulation site 122. The refilling method is in fact a molding fabrication technique, and therefore, polymers can be another option as the refilling material, which can result in rapid and low cost fabrication of neural probes. In this case, the mold can be reused which reduces the cost of fabrication. Other lining/filling methods are certainly possible, but it is preferable if the method facilitates conformal deposition in the high-aspect-ratio axial trenches 156.

Figure 13:
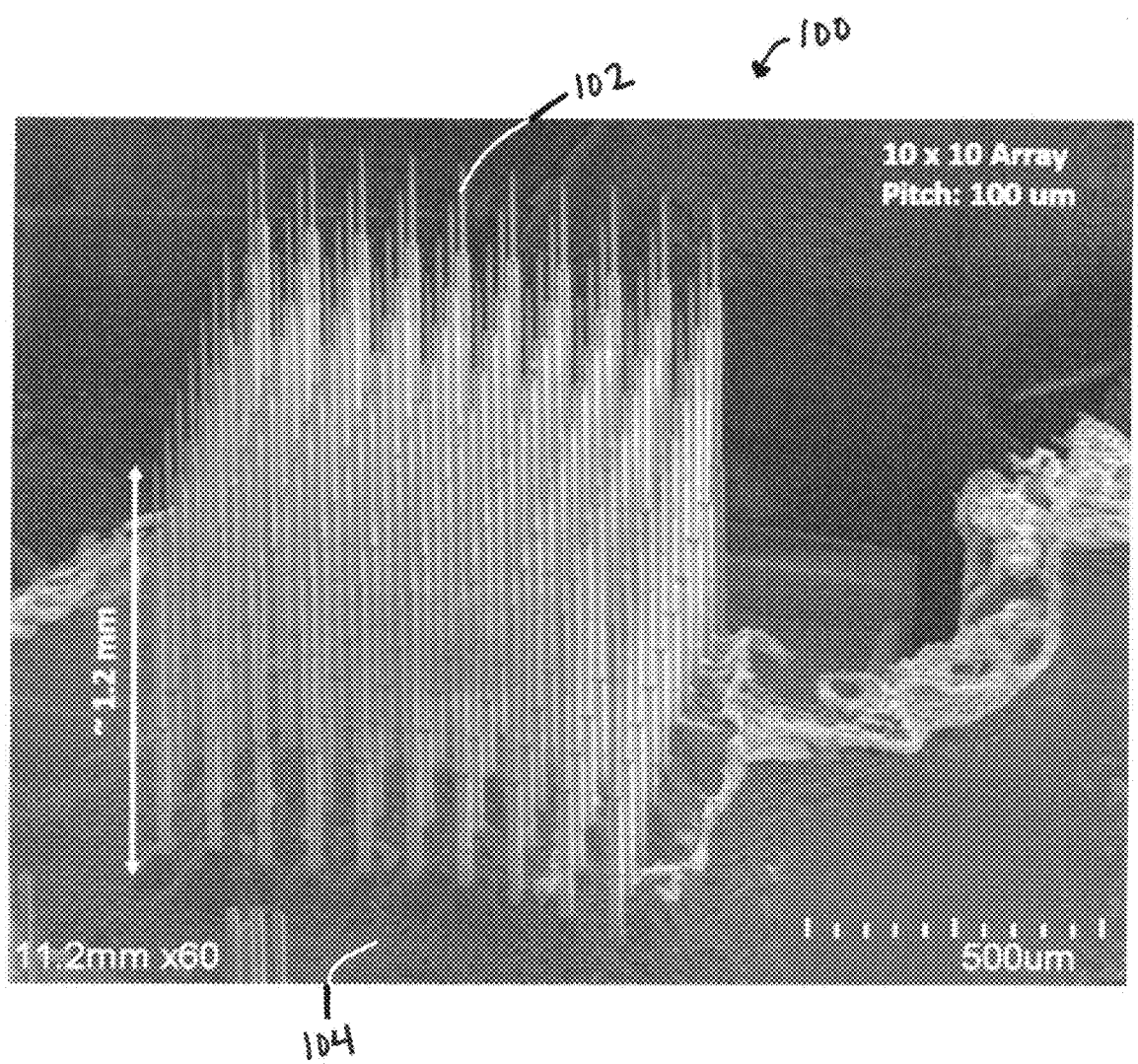
FIG. 13 is an SEM image of a probe array according to one embodiment that was manufactured using the method of FIGS. 11A-11E.
Figure 14:
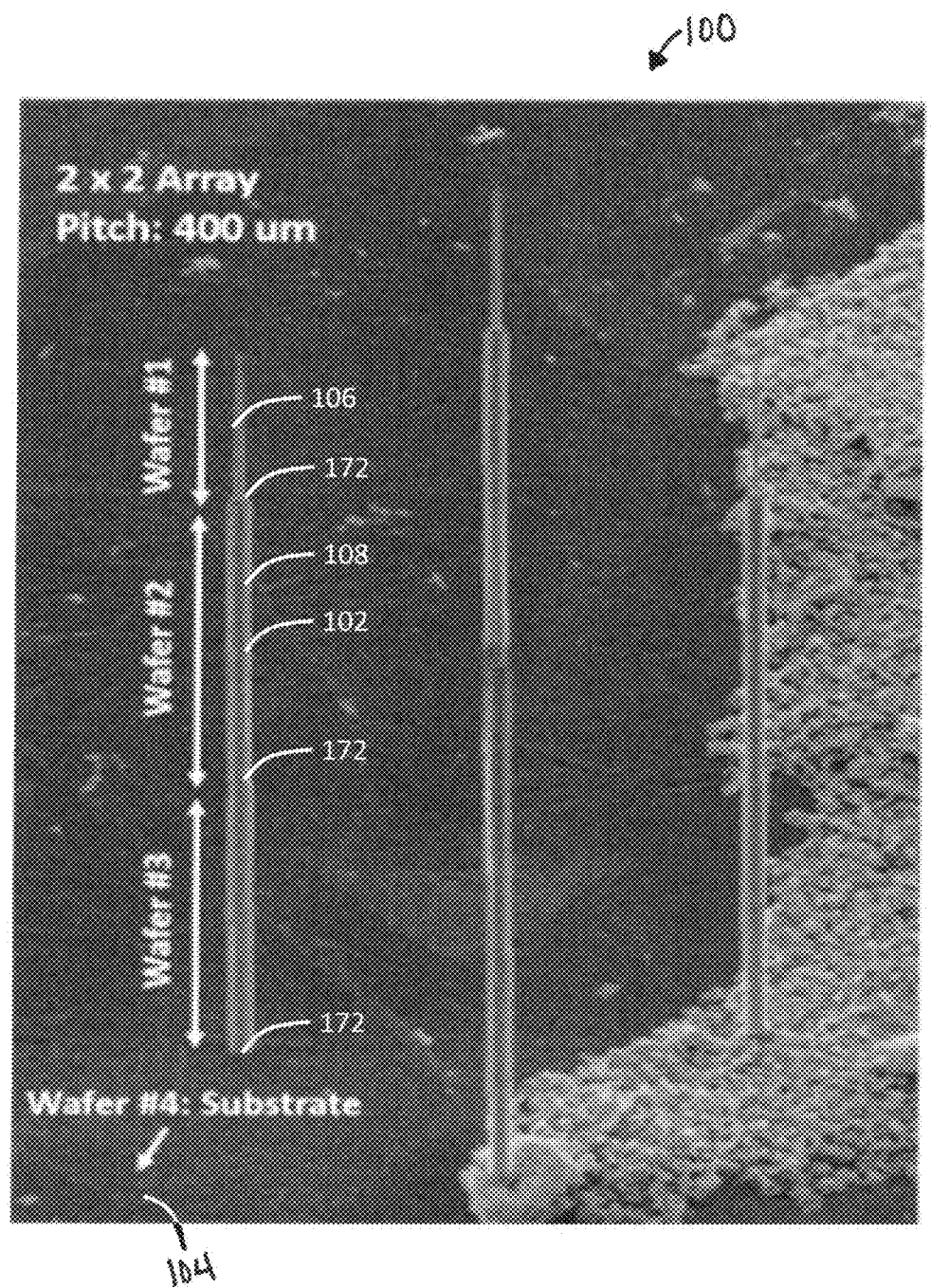
FIG. 14 is an SEM image of a probe array according to the embodiment of FIG. 13, showing a few enlarged probes.

FIGS. 13 and 14 illustrate probe arrays 100 formed by the method depicted in FIGS. 11A-11E. FIG. 13 includes probes 102 formed by bonding four 500 μm thick silicon wafers using fusion bonding to obtain axial trenches 156 of about 1.7 mm. As will be apparent, depending on the thickness of the wafer 150, the size of the axial trench 156 will vary. In one embodiment, the wafers 150 each have a thickness of about 100-900 μm, and between about two and twenty wafers 150 are aligned and joined to produce the axial trenches to form the probe array. For longer probes 102, more wafers 150 may be joined. In the more particular embodiment illustrated in FIGS. 13 and 14, 1.2 mm long probe arrays 100 with various numbers of shanks, pitch and size are realized by etching the top three silicon wafers 150 away and leaving the bottom wafer 150 as the substrate 104. Accordingly, as shown more particularly in FIG. 14, alignment junction portions 172 are formed, one of which being at the junction of the shank portion 108 and the substrate 104, and another of which defining the electrode tip portion 106.

Figure 15A:
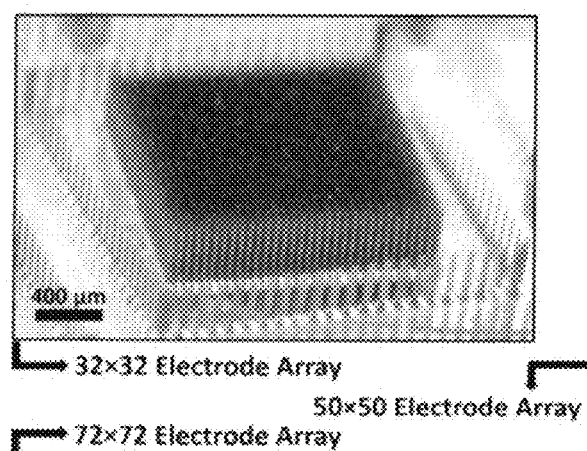
FIGS. 15A-15C are images illustrating the scalability of the various manufacturing methods.
Figure 15B:
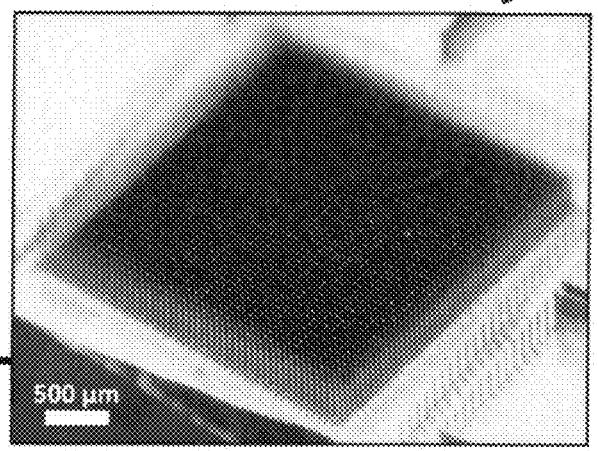
Figure 15C:
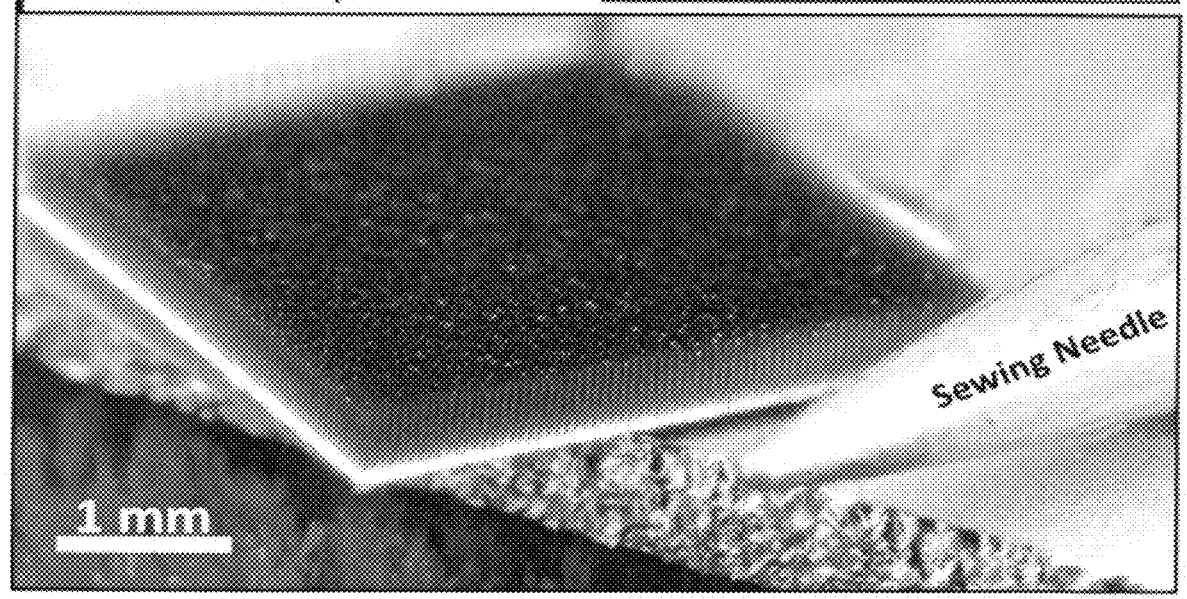

FIGS. 15A-15C illustrate the scalability of the methods of manufacture disclosed herein. Scalability of this technology is demonstrated by fabricating arrays with various electrode counts. FIG. 15A is an optical image of a 32×32 probe array 100. FIG. 15B is an optical image of a 50×50 probe array 100. FIG. 15C is an optical image of a 72×72 probe array 100. In each of FIGS. 15A-15C, the probe pitch or spacing is about 50 μm, the probe length is about 500 μm, the probe thickness or diameter at the base or substrate is about 20 μm, and the thickness or diameter at the tip end is less than 2 μm.

FIGS. 16A-16E are SEM images of an embodiment of an electrode tip portion 106 having metallized recording/stimulation sites 122 at both the tip end 110 and the proximal facing shoulder 112. FIG. 16A shows a single probe 102 having a gold electroplated recording/stimulation site 122 at the proximal facing shoulder 112. FIG. 16B is a close-up of the tip end 110, in an embodiment in which the tip end 110 is not metallized such that the proximal facing shoulder 112 is selectively metallized. FIG. 16C shows the recording/stimulation site 122 at the proximal facing shoulder, which in this embodiment, has a surface area greater than about 300 μm². FIG. 16D shows the interface between the electroplated gold layer and the probe sidewall ONO layer at the shank portion 108. FIG. 16E shows an embodiment in which metallization of the tip end 110 is obtained by increasing the ONO etching time to remove the ONO at the tip end 110 and expose the n-type polysilicon.

The method illustrated in FIGS. 17A-17E may be used to form the recording/stimulation sites 122 depicted in FIGS. 16A-16E. In FIG. 17A, the probe 102 is protected by the outer ONO dielectric layer 160 after dissolving the silicon wafer 150 and sacrificial polysilicon by EDP etching. In FIG. 17B, the ONO layer 160 is removed from the proximal facing shoulder 112 using a highly direction-dependent RIE process to expose the underlying n-type polysilicon conductive layer 162. This etching step duration should be optimized to make sure ONO etching occurs locally at the proximal facing shoulder 112 and that the rest of the probe 102 remains insulated by the ONO dielectric layer. In FIG. 17C, a metal seed layer 174 (e.g., Cr/Au) is deposited using an evaporation technique. The seed layer 174 may be about 300-1000 A° in one embodiment. Evaporation is used to exploit line-of-sight deposition (e.g., poor step coverage) to avoid deposition on the probe sidewalls. In FIG. 17D, gold, for example, is electroplated over the exposed n-type polysilicon layer 162 coated with seed layer 174. In one embodiment, electroplating is done with current density of about 1.27 mA/cm² for 2 minutes. Gold can help reduce impedance (such as by increasing the surface roughness which results in an increased surface area), but any operable material may be used for the recording/stimulation site 122. In this embodiment, electroplating does not occur at the tip end 110, since the conductive core 162 of n-type polysilicon is not exposed. In FIG. 17E, wet etching removes the excess seed layer 174 from the rest of the probe array to avoid any electrical short circuit. This method results in a recording/stimulation site 122 at the proximal facing shoulder 112, and its larger surface area than the tip end 110 can help reduce impedance. Moreover, the structure of the proximal facing shoulder 112 allows for a simplified, self-aligned site metallization process which uses a direction-dependent reactive ion etching (RIE) and metal deposition, thereby circumventing typical lithography steps.

Figure 18B:
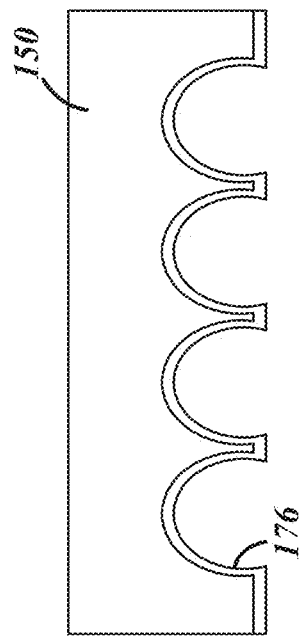
FIGS. 18A-18D illustrate a method of forming a tip end of a probe for a probe array.
Figure 18D:
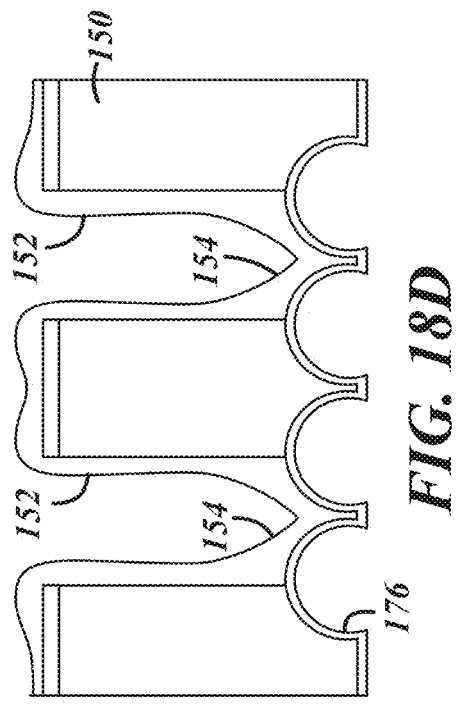
Figure 18A:
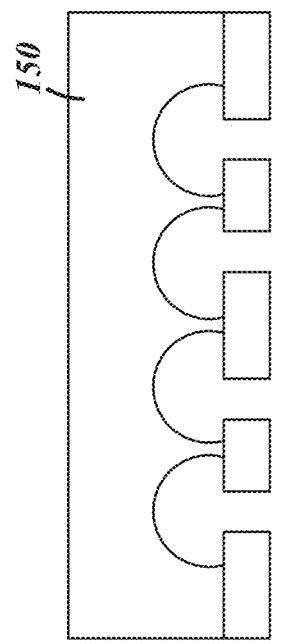
Figure 18C:
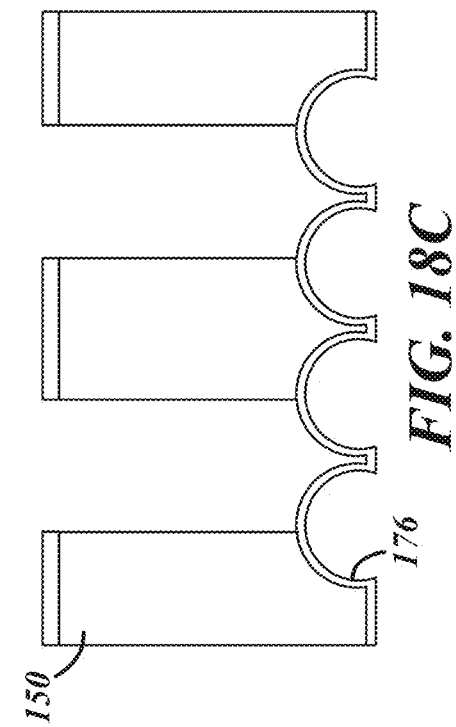

FIGS. 18A-18D illustrate an embodiment of forming a tapered end portion 154 for forming a sharp tip end 110. FIG. 18A shows isotropic etching of the backside of the silicon wafer 150. FIG. 18B shows oxidation of the wafer 150 to form a DRIE etch stop layer 176. FIG. 18C shows through-wafer DRIE etch stopped by the oxide etch stop layer 176. FIG. 18D shows a refilling process to form the body segment channels 152 and the tapered end portions 154.

FIGS. 19A-19F show another embodiment for manufacturing a probe array 100 using a reverse DRIE process (i.e., DRIE etching of probes 102 in the silicon wafer). In FIG. 19A, an electrode wafer 178 and an interconnection wafer 180 are prepared. In one embodiment, the electrode wafer 178 is diffused with boron, and the interconnection wafer 180 is etched by DRIE to form holes or axial trenches, with dielectric and in-situ doped polysilicon LPCVD probe material layers. The electrode wafer 178 should be bonded to another silicon or glass wafer prior to the DRIE, since isolated islands of silicon pillars are needed to make sure the probes 102 are electrically isolated. In FIG. 19B, the electrode wafer 178 and the interconnection wafer 180 are bonded, such as with fusion bonding. In FIG. 19C, the electrode wafer 178 is patterned, and the electrode tip portions 106 are formed by a RIE 3D etching. In FIG. 19D, the shank portions 108 are formed by a through-wafer DRIE, etching the whole wafer 178 and leaving vertical silicon pillars. In FIG. 19E, boron diffusion is used to dope the silicon pillar sidewalls to electrically connect the tip portion to its corresponding shank portion. Additionally, an LPCVD SiO₂ insulation layer 160 is formed, followed by etching the SiO₂ to expose the doped silicon conductive core layer 162 at the tip end 110. In FIG. 19F, the tip ends 110 are metallized to form recording/stimulation sites 122, and the backside of the interconnection wafer 180 is patterned to form connection or contact pads 166.

FIGS. 20, 21, and 22A-22C illustrate the optical probe 102a for optogenetics applications and manufacture of the probe 102a to form a waveguide core 144 for transmitting light from a light source. Typically, with reference to FIGS. 20 and 21, the waveguide 144 and optical fiber cladding or outer insulator 160 can be formed by using materials with different refractive indexes in the refilling stack. Also, waveguides 144 can be easily formed by using popular microfabrication materials such as LPCVD oxide (SiO₂) and an oxynitride (SiON) layer to add optical recording and stimulation and optogenetics functionality to the probe array 100. FIG. 20 schematically depicts the waveguide concept which is based on the total internal reflection of the light in occurring at the interface of two materials with different refractive indexes. FIG. 21 shows the realization of waveguides 144 for optogenetics applications, using a particular fabrication technology, one embodiment of which is depicted in FIGS. 22A-22C. In FIG. 21, light rays 145 are subject to total internal reflection within a SiON core, which is surrounded by a SiO₂ cladding 160. In the fabrication schematic of FIG. 22A, the wafer 150 has a body segment channel 152 and tapered end portion 154 forming an axial trench 156. Forming the axial trench 156 may be accomplished as described with respect to FIGS. 10A-10E or 11A-11E, for example. In FIG. 22B, the probe material layers 144, 160 are deposited. This embodiment also includes a hollow core 182. FIG. 22C shows the optical probe 102*a* which includes the hollow core 182, the waveguide 144 and the outer insulator layer 160. The outer layer 160 is etched away at the tip end 110 to facilitate light transmission out of the waveguide 144.

Figure 23:
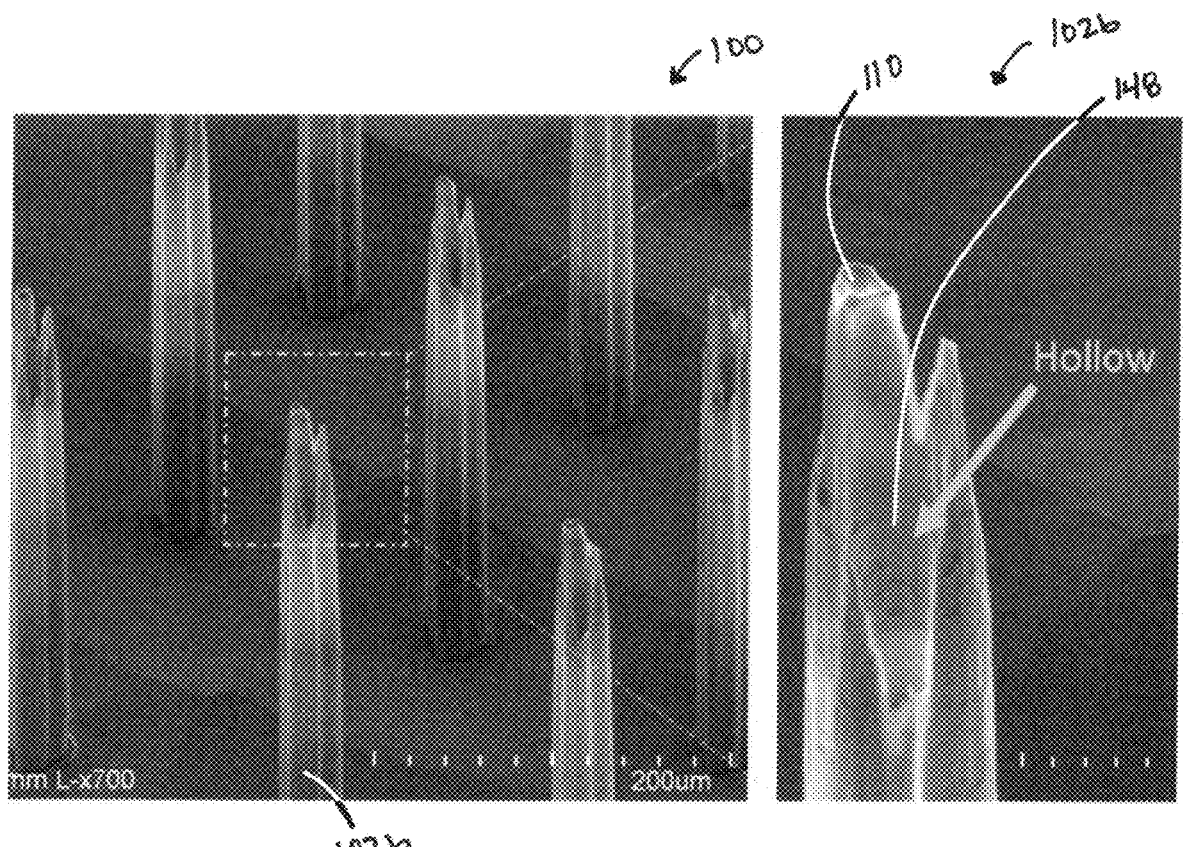
FIG. 23 is an SEM image of one embodiment of a probe array and probe.
Figure 24A:
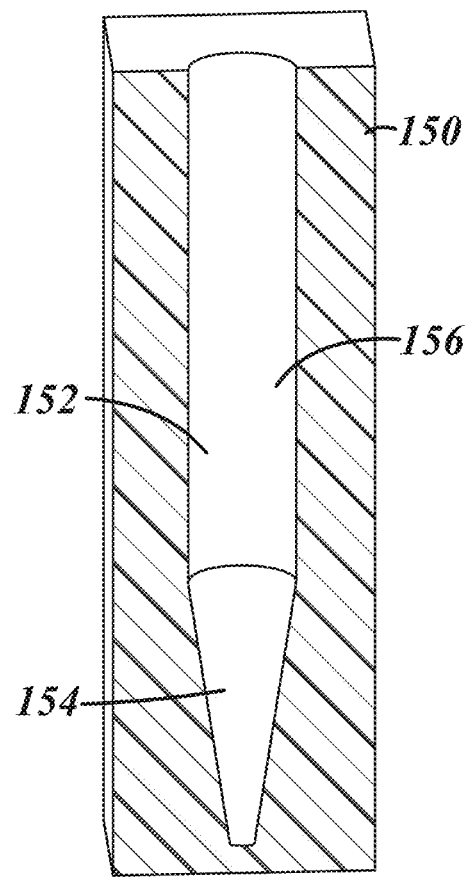
FIGS. 24A-24C illustrate a method of manufacturing the probe of FIG. 23.
Figure 24B:
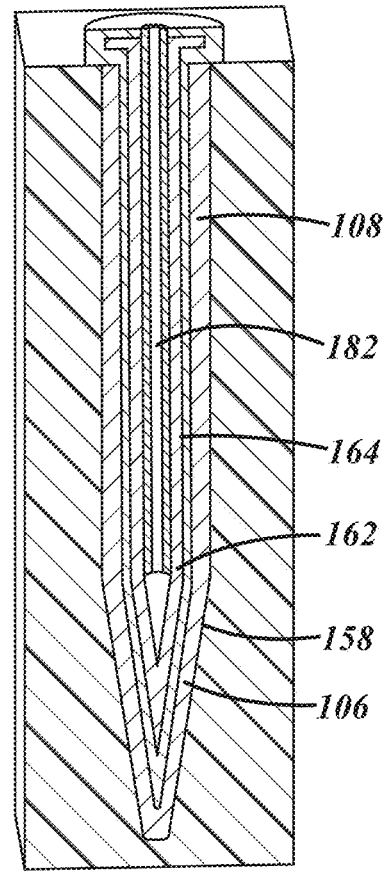
Figure 24C:
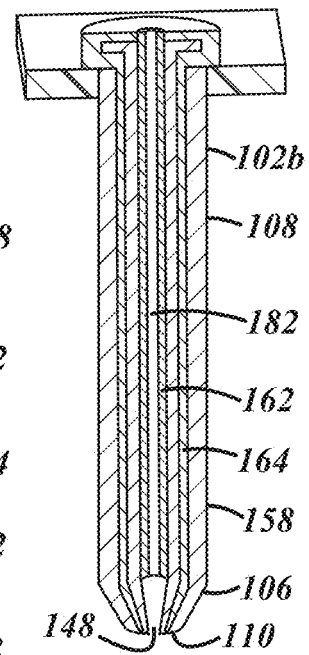

FIGS. 23 and 24A-24C show a chemical sensing and/or delivery probe 102*b* and an associated method of manufacture. FIG. 23 is an SEM image of a probe array 100 having a plurality of chemical sensing and/or delivery probes 102*b*. The chemical sensing and/or delivery probe 102*b* includes a microfluidic channel 148. In one embodiment, the microfluidic channel 148 is formed at the tip end 110 by layout engineering. In FIG. 24A, the axial trench 156 is formed, for example, using the methods of FIGS. 10A-10E or 11A-11E. If the diameter of the axial trench 156 exceeds about double or more of the deposited refilling layer thickness, the trench will not be refilled completely and will leave a hollow core 182 in the center of the probe 102*b*. This hollow core 182, as shown in FIG. 24B, helps form the microfluidic channel 148. In FIG. 24C, additional RIE etching of the tip end 110 forms the microfluidic channel 148 which provides access to the hollow core 182 for chemical or drug delivery.

Figure 26A:
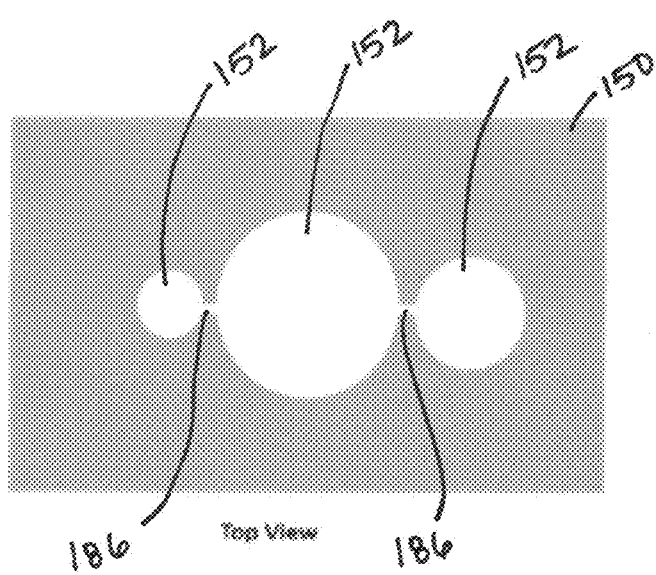
FIGS. 26A and 26B illustrate a body segment channel for forming a probe, and an illustration of the formed probe, respectively.
Figure 26B:
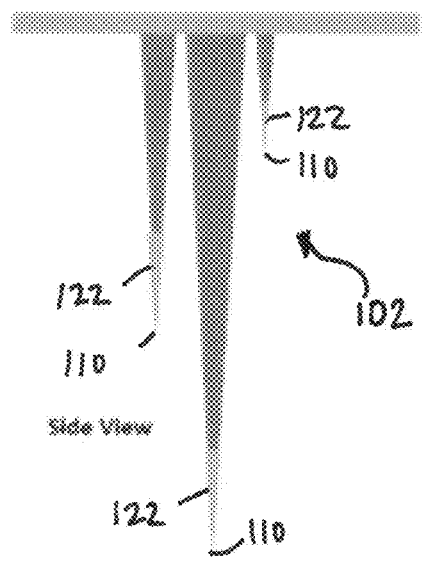
Figure 27:
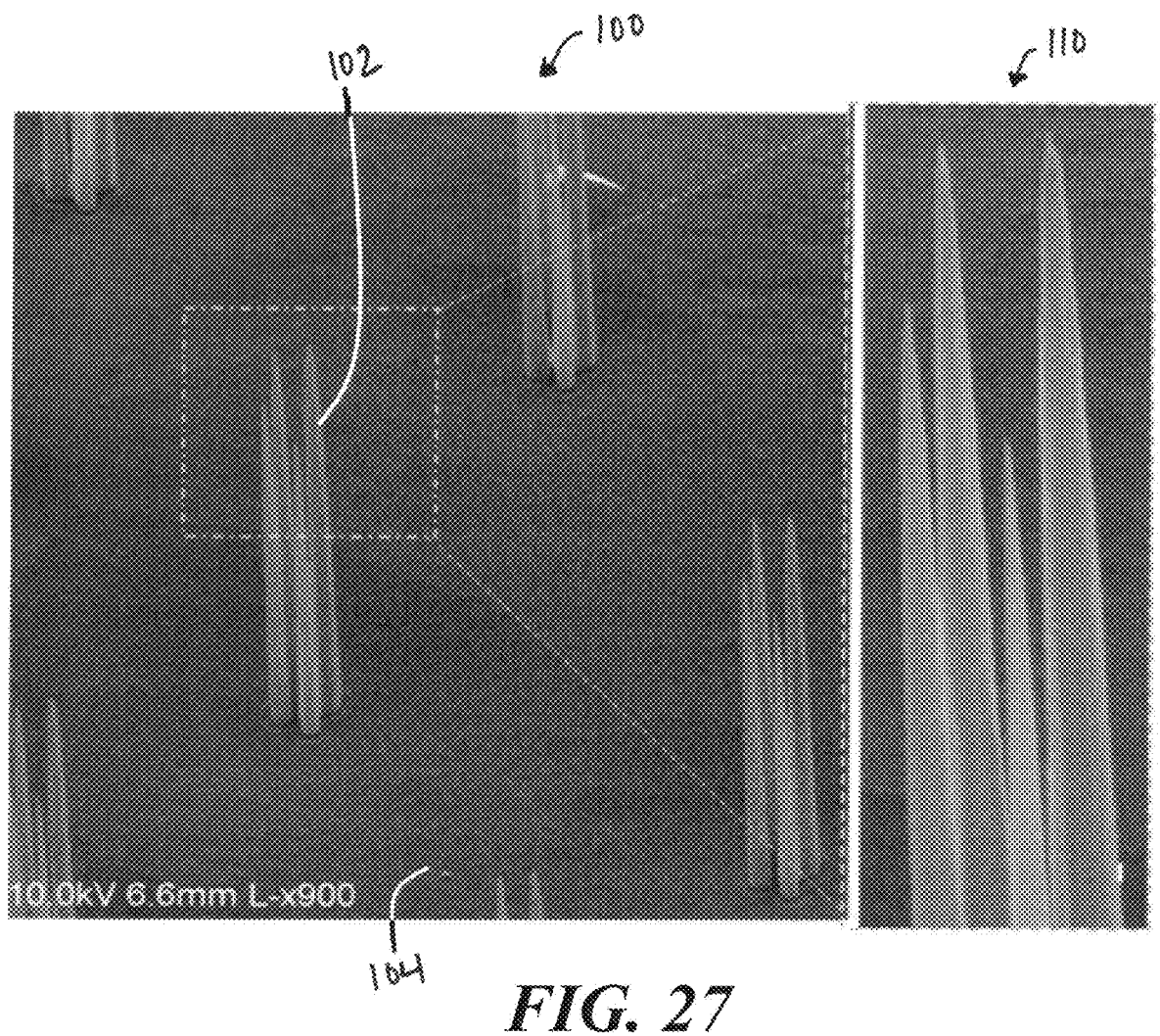
FIG. 27 is an SEM image of a probe array and probe formed with the body segment channel of FIG. 26A.

FIGS. 25A, 25B, 26A, 26B, and 27 show embodiments of realizing multiple recording/stimulation sites 122 per probe 102. FIGS. 25A and 25B show one embodiment in which multiple body segment channels 152 of differing diameters have an overlapping type of configuration. The various body segment channels 152 may be isolated by silicon walls 184 to provide electrical isolation or channels may be isolated by the deposited dielectric layers such as ONO. Using an ARDE DRIE effect, multiple sharp tips for recording sites 122 will form at various depths due to the ARDE nature of DRIE. The number of recording sites 122 per probe 102 is determined by the number of body segment channels 152 that are laid out along the perimeter of the main body segment channel for the main probe shank. FIGS. 26A and 26B illustrate another embodiment in which the body segment channels 152 are connected with small connecting passageways 186. The connecting passageways 186 are channels (e.g., less than 7 μm in diameter) that are narrow, yet wide enough to be fully refilled by the sacrificial polysilicon LPCVD, and therefore, can provide isolation of the sites 122 formed around the shank of the main probe 102. FIG. 27 is an SEM image of a fabricated 4-site per probe 102 using the approach of FIGS. 26A and 26B. The size of the probe tip ends 110 are sub-micron, and the shank diameter at the substrate 104 is about 20 μm. With the embodiments described in FIGS. 25A, 25B, 26A, 26B, and 27, it is feasible to realize multi-sites for recording and stimulation per probe 102, which greatly increases the density of recording/stimulation sites per implanted volume and enables neural recording and stimulation from various tissue layers.

Figure 28:
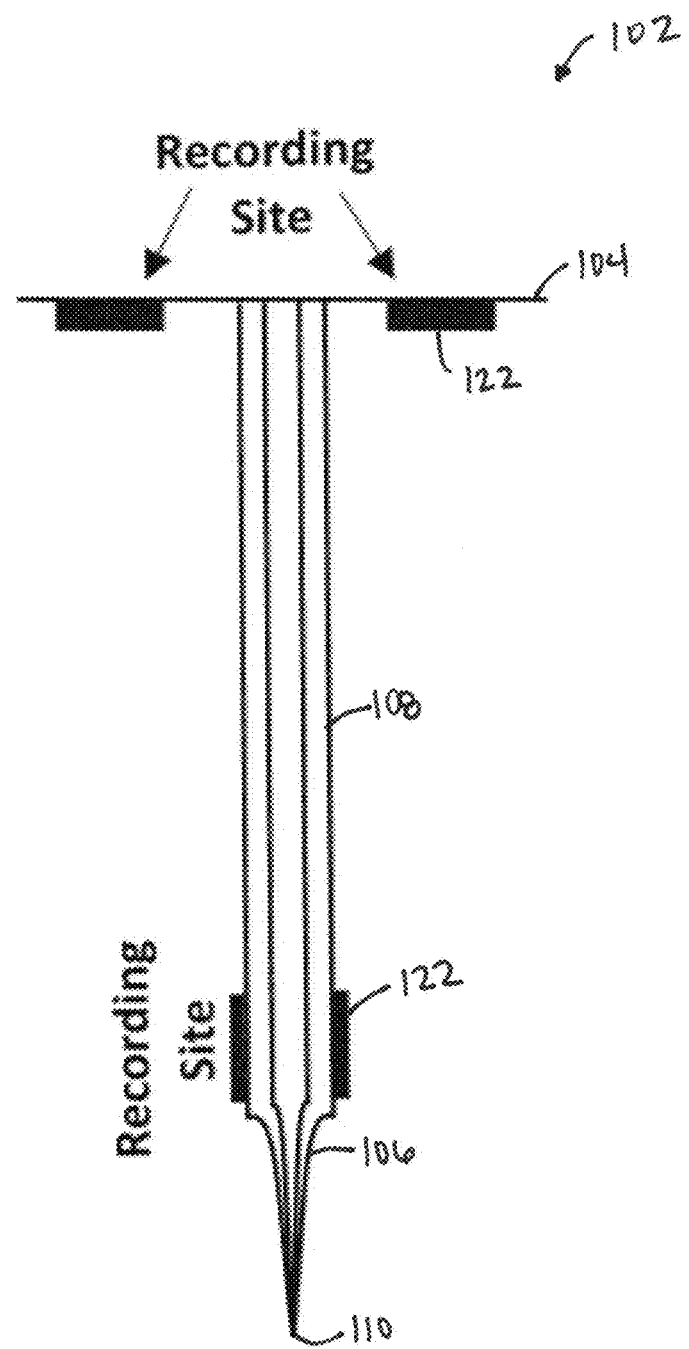
FIG. 28 is another embodiment of a probe for a probe array.

FIG. 28 illustrates another embodiment of a multi-recording/stimulation site probe 102. This embodiment has two sets of recording/stimulation sites 122. The recording/stimulation site 122 on the substrate 104 can be an ECoG-type site to record electrophysiological signals from the surface of the brain, along with another recording/stimulation site 122 along the penetrating probe shank portion 108 to record from the depth of the brain and neural structures. As described above, this probe embodiment may also include other modalities such as optical and/or chemical and drug delivery.

FIGS. 29A and 29B illustrate yet another multi-recording/stimulation site probe 102, taking advantage of the flat shoulders formed as a result of a gradual reduction in diameters of the body segment channels 152 and bonding alignment tolerance of the wafers 150. Recording sites 122 are formed using, for example, the technique described in FIGS. 17A-17E. In this embodiment, the recording sites 122 are formed at alignment junction portions 172 where the diameter of the probe shank portion 108 changes. Accordingly, in this embodiment, the shank portion 108 includes a plurality of proximal facing shoulders 112.

FIGS. 30A-30C show probes with differently shaped and sized tip ends 110. Two techniques may be used to control the shape and size of the tip end 110: sacrificial layer thickness and/or DRIE lag effect. Increasing the sacrificial layer thickness reduces the final probe tip end diameter and increases the tip end sharpness. Sharper tip ends can also be obtained using smaller hole diameters to enhance the DRIE lag effect which increases the hole etching sidewall profile slope, resulting in sharper tip ends. Using the combination of above approaches can result in tip end size ranging from tens of nanometers to sub-micrometer.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation. In addition, the term "and/or" is to be construed as an inclusive OR. Therefore, for example, the phrase "A, B, and/or C" is to be interpreted as covering all the following: "A"; "B"; "C"; "A and B"; "A and C"; "B and C"; and "A, B, and C."

The invention claimed is:

1. A method of manufacturing a probe array, comprising steps of:
   etching a plurality of substrates to form a plurality of body segment channels;
   stacking the plurality of substrates to at least partially align the plurality of body segment channels in each substrate of the plurality of substrates to form a plurality of axial trenches, wherein each axial trench is a hollow hole comprised of aligned body segment channels from two or more substrates of the plurality of substrates;
   at least partially filling the axial trenches with one or more layers of probe material to form probes; and
   separating the probes from the plurality of substrates.

2. The method of claim 1, wherein the filling step involves gas-phase deposition.

3. The method of claim 1, wherein the filling step involves metal electroplating.

4. The method of claim 1, wherein the filling step involves using a polymer probe material.

5. The method of claim 1, wherein the number of body segment channels are not the same in one or more of the plurality of substrates such that at least some axial trenches have different axial trench lengths.

6. The method of claim 1, wherein one or more body segment channels have different diameters such that one or more axial trenches have a variable depth axial diameter.

7. The method of claim 1, wherein the etching step comprises aspect ratio dependent etching (ARDE) that involves a deep reactive ion etching (DRIE) lag effect that at least partially forms at least some body segment channels in one or more substrates of the plurality of substrates with a tapered end portion.

8. The method of claim 1, wherein the substrate has a first side and an opposite second side and the etching step comprises the steps of:
isotropic etching of the first side of at least one substrate of the plurality of substrates; and
etching through the opposite second side using through-substrate deep reactive ion etching (DRIE).

9. A method of manufacturing a probe array for electrophysiological recording/stimulation, comprising steps of:
etching a plurality of substrates to form a plurality of body segment channels;
at least partially aligning the plurality of body segment channels in each substrate of the plurality of substrates to form a plurality of axial trenches, wherein at least some of the body segment channels are at least partially overlapping;
at least partially filling the axial trenches with one or more layers of probe material to form one or more probes with multiple recording/stimulation sites; and
separating the probes from the plurality of substrates.

10. A method of manufacturing a probe array for electrophysiological recording/stimulation, comprising steps of:
etching a plurality of substrates to form a plurality of body segment channels;
at least partially aligning the plurality of body segment channels in each substrate of the plurality of substrates to form a plurality of axial trenches, wherein at least some of the body segment channels are connected by one or more connecting passageways;
at least partially filling the axial trenches with one or more layers of probe material to form one or more probes with multiple recording/stimulation sites; and
separating the probes from the plurality of substrates.

11. The method of claim 1, wherein each substrate of the plurality of substrates has a thickness in a range of about 100-900 μm, and 2-20 substrates are at least partially aligned to create a plurality of axial trenches, each axial trench having an axial trench length of about 0.2 to 18 mm.

12. The method of claim 11, wherein each substrate of the plurality of substrates has a thickness of about 500 μm, and 4 substrates are at least partially aligned to create a plurality of axial trenches, each axial trench having an axial trench length of about 1.7 mm.

13. The method of claim 1, wherein the probe material includes a cladding layer to create a waveguide, and the probe array comprises a light source configured to transmit light through the waveguide.

14. The method of claim 1, wherein the filling step is performed to create a hollow core in one or more of the probes, and a tip end of the one or more probes is etched to form a microfluidic channel.

15. The method of claim 1, further comprising the step of bonding the plurality of aligned substrates.

16. The method of claim 1, wherein at least some of the body segment channels are grouped to form a probe cluster in the probe array.

17. A method of manufacturing a probe array, comprising steps of:
aspect ratio dependent etching (ARDE) a substrate to form a plurality of body segment channels;
using a deep reactive ion etching (DRIE) lag effect to at least partially form a plurality of axial trenches that include a tapered end portion at each of the body segment channels;
lining the plurality of axial trenches with a sacrificial layer;
at least partially filling the lined axial trenches with one or more layers of probe material to form coated probes;
separating the coated probes from the substrate; and
etching the sacrificial layer on the coated probes so that an outer diameter of each of the coated probes is diametrically reduced because of the etching of the sacrificial layer to increase an aspect ratio of each of the coated probes.

18. A method of manufacturing a probe array, comprising steps of:
etching a substrate to form a plurality of axial trenches;
lining the plurality of axial trenches with a sacrificial layer;
at least partially filling the lined axial trenches with one or more layers of probe material to form coated probes;
separating the coated probes from the substrate; and
etching the sacrificial layer on the coated probes so that an outer diameter of each of the coated probes is diametrically reduced because of the etching of the sacrificial layer to increase an aspect ratio of each of the coated probes.

19. A method of manufacturing a probe array, comprising steps of:
preparing an electrode wafer and an interconnection wafer;
bonding the electrode wafer and the interconnection wafer;
forming a plurality of electrode tip portions and shank portions in the electrode wafer after the bonding of the electrode wafer and the interconnection wafer;
etching at least part of the electrode wafer to form a plurality of shank portions corresponding to the plurality of electrode tip portions, each shank portion and corresponding electrode tip portion comprising a probe, wherein the etching is performed after the bonding of the electrode wafer and the interconnection wafer; and
electrically connecting each electrode tip portion to a proximal end of each corresponding shank portion.

20. The method of claim 19, further comprising the step of at least partially filling with an insulation layer and etching at least part of the insulation layer to form a conductive tip end.

21. The method of claim 20, further comprising the step of metallizing the conductive tip end.

22. The method of claim 19, further comprising the step of patterning a distal end of the interconnection wafer to form a contact pad for each probe.

23. The method of claim 1, further comprising the steps of at least partially filling the plurality of axial trenches with a sacrificial layer and etching the sacrificial layer.

24. The method of claim 1, further comprising the step of at least partially filling with an insulation layer and etching at least part of the insulation layer to form a conductive tip end.

25. The method of claim 18, further comprising the step of at least partially filling with an insulation layer and etching at least part of the insulation layer to form a conductive tip end.

26. The method of claim 25, further comprising the step of metallizing the conductive tip end.

27. The method of claim 18, wherein the substrate is a single substrate.

\* \* \* \* \*